United States Patent
Jiao et al.

(10) Patent No.: US 7,553,841 B2
(45) Date of Patent: Jun. 30, 2009

(54) AMINO CYCLOBUTYLAMIDE MODULATORS OF CHEMOKINE RECEPTOR ACTIVITY

(75) Inventors: Richard Jiao, Collingswood, NJ (US); Lihu Yang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 538 days.

(21) Appl. No.: 10/549,739

(22) PCT Filed: Mar. 15, 2004

(86) PCT No.: PCT/US2004/007792

§ 371 (c)(1),
(2), (4) Date: Sep. 19, 2005

(87) PCT Pub. No.: WO2004/082682

PCT Pub. Date: Sep. 30, 2004

(65) Prior Publication Data

US 2006/0211722 A1  Sep. 21, 2006

Related U.S. Application Data

(60) Provisional application No. 60/456,047, filed on Mar. 18, 2003.

(51) Int. Cl.
*A61K 31/44* (2006.01)
*C07D 491/10* (2006.01)
(52) U.S. Cl. .................................... 514/278; 546/17
(58) Field of Classification Search .............. 546/17; 514/278
See application file for complete search history.

(56) References Cited

U.S. PATENT DOCUMENTS 6,743,794 B2  6/2004  Bonjouklian et al.

FOREIGN PATENT DOCUMENTS

| WO | WO01/22919 | * | 4/2001 |
|---|---|---|---|
| WO | WO 02/13824 | | 2/2002 |
| WO | WO 2004/110376 | | 12/2004 |

OTHER PUBLICATIONS

Abbadie et al. "CCR-2 antagonists . . . " CA 142:69197 (2004).*
Sekiya et al. "Preparation of alpha imidazolobenzoyl . . . " CA 119:203414 (1993).*
Cohen et al. "Cytokine function" Am. J. Clin. path. v.105(5) p. 589-598 (1996).*
Yang et al. "Disovery of 2-piperidinyl . . . " J. Med. Chem. v.50, p. 2609-2611 (1997).*

* cited by examiner

*Primary Examiner*—Celia Chang
(74) *Attorney, Agent, or Firm*—James L. McGinnis; Mark R. Daniel

(57) ABSTRACT

The present invention is directed to compounds of the formulas I and II: wherein $R^1$, $R^2$, $R^3$, $R^4$, $R^5$, $R^6$, $R^7$, $R^8$, $R^9$, $R^{10}$, $R^{15}$, $R^{16}$, $R^{17}$, $R^{18}$, $R^{19}$, $R^{25}$, $R^{26}$, Y, Z, l, m, n and the broken lines are as defined herein which are useful as modulators of chemokine receptor activity. In particular, these compounds are useful as modulators of the chemokine receptor CCR-2.

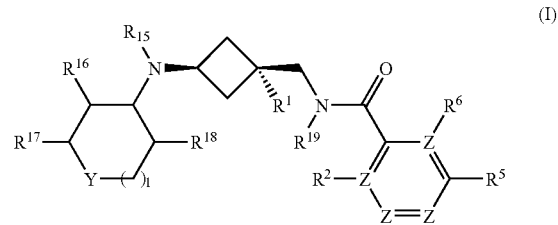

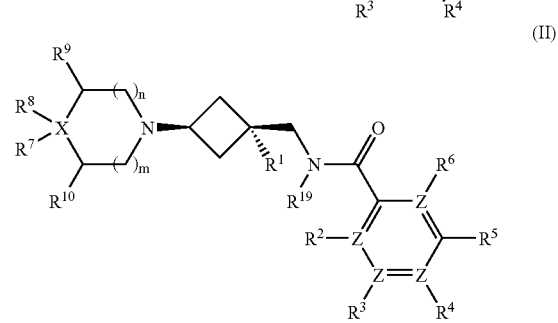

12 Claims, No Drawings

US 7,553,841 B2

AMINO CYCLOBUTYLAMIDE MODULATORS OF CHEMOKINE RECEPTOR ACTIVITY

CROSS REFERENCE TO RELATED APPLICATIONS

This application is the National Stage of International Application No. PCT/US2004/007792, filed 15 Mar. 2004 which claims the benefit under 35 U.S.C. 119(e) of U.S. Provisional Application No. 60/456,047, filed 18 Mar. 2003.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, Cytokine, 3, 165-183 (1991) and Murphy, Rev. Immun., 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., Nature, 381, 661-666 (1996)).

The chemokines are secreted by a wide variety of cell types and bind to specific G-protein coupled receptors (GPCRs) (reviewed in Horuk, Trends Pharm. Sci., 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., J. Biol. Chem., 270, 22123-22128 (1995); Beote, et al, Cell, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., Blood, 90, 908-928 (1997)); CCR-4 (or "CKR4" or "CC-CKR-4") [MIP-1α, RANTES, MCP-1] (Rollins, et al., Blood, 90, 908-928 (1997)); CCR-5 (or "CKR-5" or "CC-CKR-5") [MIP-1α, RANTES, MIP-1β] (Sanson, et al., Biochemistry, 35, 3362-3367 (1996)); and the Duffy blood-group antigen [RANTES, MCP-1] (Chaudhun, et al., J. Biol. Chem., 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., Arthritis & Rheumatism, 42, 989-992 (1999)). A review of the role of eosinophils in allergic inflammation is provided by Kita, H., et al., J. Exp. Med. 183, 2421-2426 (1996). A general review of the role of chemokines in allergic inflammation is provided by Lustger, A. D., New England J. Med., 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and Listeria monocytogenes infection (Lu et al., J. Exp. Med., 187, 601-608 (1998); Kurihara et al. J. Exp. Med., 186, 1757-1762 (1997); Boring et al. J. Clin. Invest., 100, 2552-2561 (1997); Kuziel et al. Proc. Natl. Acad. Sci., 94, 12053-12058 (1997)). Furthermore, these animals show reduced monocyte infiltration into granulomatous lesions induced by the injection of schistosomal or mycobacterial antigens (Boring et al. J. Clin. Invest., 100, 2552-2561 (1997); Warmington et al. Am J. Path., 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 −/− or CCR2 −/− mice backcrossed to APO-E −/−, LDL-R −/− or Apo B transgenic mice maintained on high fat diets (Boring et al. Nature, 394, 894-897 (1998); Gosling et al. J. Clin. Invest., 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I and of formula II:

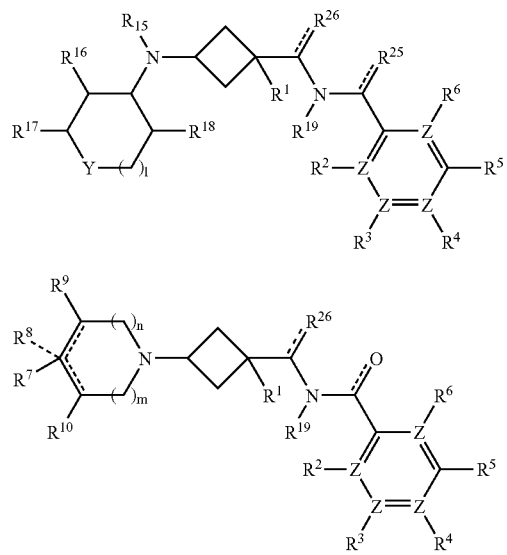

wherein:

X is selected from O, N, S, $SO_2$, or C.

Y is selected from:
—O—, $-NR^{12}-$, —S—, —SO—, $-SO_2-$, and $-CR^{12}R^{12}-$, $-NSO_2R^{14}-$, $-NCOR^{13}-$, $-CR^{12}COR^{11}-$, $-CR^{12}OCOR^{13}-$, —CO—, $R^{11}$ is independently selected from: hydroxy, hydrogen, $C_{1-6}$ alkyl, $-O-C_{1-6}$alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, $-CO_2H$, $-CO_2-C_{1-6}$ alkyl, and trifluoromethyl;

$R^{12}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, $-CO_2H$, $-CO_2-C_{1-6}$ alkyl, and trifluoromethyl;

$R^{13}$ is selected from: hydrogen, $C_{1-6}$ alkyl, $-O-C_{1-6}$ alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, $-CO_2H$, $-CO_2-C_{1-6}$ alkyl, and trifluoromethyl;

$R^{14}$ is selected from: hydroxy, $C_{1-6}$ alkyl, $-O-C_{1-6}$ alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, $-CO_2H$, $-CO_2-C_{1-6}$ alkyl, and trifluoromethyl;

Z is independently selected from C or N, where at most two of the Z are N.

$R^1$ is selected from:
hydrogen, $-C_{1-6}$alkyl, $-C_{0-6}$alkyl-O-$C_{1-6}$alkyl, $-C_{0-6}$alkyl-S-$C_{1-6}$alkyl, $-(C_{0-6}$alkyl$)-(C_{3-7}$cycloalkyl$)-(C_{0-6}$alkyl), hydroxy, heterocycle, —CN, $-NR^{12}R^{12}$, $-NR^{12}COR^{13}$, $-NR^{12}SO_2R^{14}$, $-COR^{11}$, $-CONR^{12}R^{12}$,
and phenyl;
the alkyl and the cycloalkyl are unsubstituted or substituted with 1-7 substituents where the substituents are independently selected from:
(a) halo,
(b) hydroxy,
(c) $-O-C_{1-3}$alkyl,
(d) trifluoromethyl,
(f) $C_{1-3}$alkyl,
(g) $-O-C_{1-3}$alkyl,
(h) $-COR^{11}$,
(i) $-SO_2R^{14}$,
(j) $-NHCOCH_3$,
(k) $-NHSO_2CH_3$,
(l) -heterocycle,
(m) =O,
(n) —CN,
and where the phenyl and heterocycle are unsubstituted or substituted with 1-3 substituents where the substituents are independently selected from: halo, hydroxy, $-COR^{11}$, $C_{1-3}$alkyl, $C_{1-3}$alkoxy and trifluoromethyl;

$R^2$ is selected from:
(a) hydrogen,
(b) $C_{1-3}$alkyl, optionally substituted with 1-3 fluoro,
(c) $-O-C_{1-3}$alkyl, optionally substituted with 1-3 fluoro,
(d) hydroxy,
(e) chloro,
(f) fluoro,
(g) bromo,
(h) phenyl,
(g) heterocycle, and
(h) nothing or O (when the Z bonded to $R^2$ is N);

$R^3$ is selected from:
(a) hydrogen,
(b) $C_{1-3}$alkyl, optionally substituted with 1-3 fluoro,
(c) $-O-C_{1-3}$alkyl, optionally substituted with 1-3 fluoro,
(d) hydroxy,
(e) chloro,
(f) fluoro,
(g) bromo,
(h) phenyl,
(g) heterocycle, and
(h) nothing or O (when the Z bonded to $R^3$ is N);

$R^4$ is selected from:
(a) hydrogen,
(b) $C_{1-3}$alkyl, optionally substituted with 1-3 fluoro,
(c) —O—$C_{1-3}$alkyl, optionally substituted with 1-3 fluoro,
(d) hydroxy,
(e) chloro,
(f) fluoro,
(g) bromo,
(h) phenyl,
(g) heterocycle, and
(h) nothing or O (when the Z bonded to $R^4$ is N);
$R^5$ is selected from:
(a) $C_{1-6}$alkyl, where alkyl may be unsubstituted or substituted with 1-6 fluoro and optionally substituted with hydroxyl,
(b) —O—$C_{1-6}$alkyl, where alkyl may be unsubstituted or substituted with 1-6 fluoro,
(c) —CO—$C_{1-6}$alkyl, where alkyl may be unsubstituted or substituted with 1-6 fluoro,
(d) —S—$C_{1-6}$alkyl, where alkyl may be unsubstituted or substituted with 1-6 fluoro,
(e) -pyridyl, which may be unsubstituted or substituted with one or more substituents selected from: halo, trifluoromethyl, $C_{1-4}$alkyl, and $COR^{11}$,
(f) fluoro,
(g) chloro,
(h) bromo,
(i) —$C_{4-6}$cycloalkyl,
(j) —O—$C_{4-6}$cycloalkyl,
(k) phenyl, which may be unsubstituted or substituted with one or more substituents selected from: halo, trifluoromethyl, $C_{1-4}$alkyl, and $COR^{11}$,
(l) —O—-phenyl, which may be unsubstituted or substituted with one or more substituents selected from: halo, trifluoromethyl, $C_{1-4}$alkyl, and $COR^{11}$,
(m) —$C_{3-6}$cycloalkyl, where alkyl may be unsubstituted or substituted with 1-6 fluoro,
(n) —O—$C_{3-6}$cycloalkyl, where alkyl may be unsubstituted or substituted with 1-6 fluoro,
(o) -heterocycle,
(p) —CN, and
(q) —$COR^{11}$;
$R^6$ is selected from:
(a) hydrogen,
(b) $C_{1-3}$alkyl, optionally substituted with 1-3 fluoro,
(c) —O—$C_{1-3}$alkyl, optionally substituted with 1-3 fluoro,
(d) hydroxy,
(e) chloro,
(f) fluoro,
(g) bromo,
(h) phenyl,
(g) heterocycle, and
(h) nothing or O (when the Z bonded to $R^6$ is N);
$R^7$ is selected from:
hydrogen, ($C_{0-6}$alkyl)-phenyl, ($C_{0-6}$alkyl)-heterocycle, ($C_{0-6}$alkyl)-$C_{3-7}$cycloalkyl, ($C_{0-6}$alkyl)-$COR^{11}$, ($C_{0-6}$alkyl)-(alkene)-$COR^{11}$, ($C_{0-6}$alkyl)-$SO_3H$, ($C_{0-6}$alkyl)-W—$C_{0-4}$alkyl, ($C_{0-6}$alkyl)-$CONR^{12}$-phenyl, ($C_{0-6}$alkyl)-$CONR^{20}$—V—$COR^{11}$, and nothing (when X is O, S, or $SO_2$), where W is selected from: a single bond, —O—, —S—, —SO—, —$SO_2$—, —CO—, —$CO_2$—, —$CONR^{12}$— and —$NR^{12}$—, and where V is selected from $C_{1-6}$alkyl or phenyl, and where the $R^{20}$ can be hydrogen, $C_{1-4}$alkyl, or where $R^{20}$ is joined via a 1-5 carbon tether to one of the carbons of V to form a ring,
and where the $C_{0-6}$alkyl is unsubstituted or substituted with 1-5 substituents, where the substituents are independently selected from:
(a) halo,
(b) hydroxy,
(c) —$C_{0-6}$alkyl
(d) —O—$C_{1-3}$alkyl,
(e) trifluoromethyl, and
(f) —$C_{0-2}$alkyl-phenyl,
and where the phenyl, heterocycle, cycloalkyl, and $C_{0-4}$alkyl is unsubstituted or substituted with 1-5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$C_{0-3}$—$COR^{11}$,
(g) —CN,
(h) —$NR^{12}R^{12}$,
(i) —$CONR^{12}R^{12}$, and
(j) —$C_{0-3}$-heterocycle,
or where the phenyl and heterocycle may be fused to another heterocycle, which itself may be unsubstituted or substituted with 1-2 substituents independently selected from hydroxy, halo, —COR11, and —$C_{1-3}$alkyl,
and where alkene is unsubstituted or substituted with 1-3 substituents which are independently selected from:
(a) halo,
(b) trifluoromethyl,
(c) $C_{1-3}$alkyl,
(d) phenyl, and
(e) heterocycle;
$R^8$ is selected from:
(a) hydrogen,
(b) nothing when X is either O, S, $SO_2$ or N or when a double bond joins the carbons to which $R^7$ and $R^{10}$ are attached,
(c) hydroxy,
(d) $C_{1-6}$alkyl,
(e) $C_{1-6}$alkyl-hydroxy,
(f) —O—$C_{1-3}$alkyl,
(g) —$COR^{11}$,
(h) —$CONR^{12}R^{12}$, and
(i) —CN;
or where $R^7$ and $R^8$ may be joined together to form a ring which is selected from:
(a) 1H-indene,
(b) 2,3-dihydro-1H-indene,
(c) 2,3-dihydro-benzofuran,
(d) 1,3-dihydro-isobenzofuran,
(e) 2,3-dihydro-benzothiofuran,
(f) 1,3-dihydro-isobenzothiofuran,
(g) 6H-cyclopenta[d]isoxazol-3-ol
(h) cyclopentane, and
(i) cyclohexane,
where the ring formed may be unsubstituted or substituted with 1-5 substituents independently selected from:
(a) halo,
(b) trifluoromethyl,
(c) hydroxy,
(d) $C_{1-3}$alkyl,
(e) —O—$C_{1-3}$alkyl,
(f) —$C_{0-3}$—$COR^{11}$,
(g) —CN, (h) —NR$^{12}$R$^{12}$,
(i) —CONR$^{12}$R$^{12}$, and
(j) —C$_{0-3}$-heterocycle,
or where R$^7$ and R$^9$ or R$^8$ and R$^{10}$ may be joined together to form a ring which is phenyl or heterocycle,
wherein the ring is unsubstituted or substituted with 1-7 substituents where the substituents are independently selected from:
(a) halo,
(b) trifluoromethyl,
(c) hydroxy,
(d) C$_{1-3}$alkyl,
(e) —O—C$_{1-3}$alkyl,
(f) —COR$^{11}$,
(g) —CN,
(h) —NR$^{12}$R$^{12}$, and
(i) —CONR$^{12}$R$^{12}$;

R$^9$ and R$^{10}$ are independently selected from:
(a) hydrogen,
(b) hydroxy,
(c) C$_{1-6}$alkyl,
(d) C$_{1-6}$alkyl-COR$^{11}$,
(e) C$_{1-6}$alkyl-hydroxy,
(f) —O—C$_{1-3}$alkyl,
(g) =O, when R$^9$ or R$^{10}$ is connected to the ring via a double bond
(h) halo;

R$^{15}$ is selected from:
(a) hydrogen, and
(b) C$_{1-6}$alkyl, which is unsubstituted or substituted with 1-3 substituents where the substituents are independently selected from: halo, hydroxy, —CO$_2$H, —CO$_2$C$_{1-6}$alkyl, and —O—C$_{1-3}$alkyl;

R$^{16}$ is selected from:
(a) hydrogen,
(b) C$_{1-6}$alkyl, where alkyl may be unsubstituted or substituted with 1-6 substituents where the substituents are selected from: fluoro, C$_{1-3}$alkoxy, hydroxy, —COR$^{11}$,
(c) fluoro,
(d) —O—C$_{1-3}$alkyl, where alkyl may be unsubstituted or substituted with 1-3 fluoro, and
(e) C$_{3-6}$ cycloalkyl,
(f) —O—C$_{3-6}$cycloalkyl,
(g) hydroxy,
(h) —COR$^{11}$,
(i) —OCOR$^{13}$,
or R$^{15}$ and R$^{16}$ may be joined together via a C$_{2-4}$alkyl or a C$_{0-2}$alkyl-O—C$_{1-3}$alkyl chain to form a 5-7 membered ring;

R$^{17}$ is selected from:
(a) hydrogen,
(b) C$_{1-6}$alkyl, where alkyl may be unsubstituted or substituted with 1-6 substituents where the substituents are selected from: fluoro, C$_{1-3}$alkoxy, hydroxy, —COR$^{11}$,
(c) COR$^{11}$,
(d) hydroxy, and
(e) —O—C$_{1-6}$alkyl, where allyl may be unsubstituted or substituted with 1-6 substituents where the substituents are selected from: fluoro, C$_{1-3}$alkoxy, hydroxy, —COR$^{11}$,
or R$^{16}$ and R$^{17}$ may be joined together by a C$_{1-4}$alkyl chain or a C$_{0-3}$alkyl-O—C$_{0-3}$alkyl chain to form a 3-6 membered ring;

R$^{18}$ is selected from:
(a) hydrogen, and
(b) C$_{1-6}$alkyl, where alkyl may be unsubstituted or substituted with 1-6 fluoro,
(c) fluoro,
(d) —O—C$_{3-6}$cycloalkyl, and
(e) —O—C$_{1-3}$alkyl, where alkyl may be unsubstituted or substituted with 1-6 fluoro,
or R$^{16}$ and R$^{18}$ may be joined together by a C$_{2-3}$alkyl chain to form a 5-6 membered ring, where the alkyl are unsubstituted or substituted with 1-3 substituents where the substiuents are independently selected from: halo, hydroxy, —COR$^{11}$, C$_{1-3}$alkyl, and C$_{1-3}$alkoxy,
or R$^{16}$ and R$^{18}$ may be joined together by a C$_{1-2}$alkyl-O—C$_{1-2}$alkyl chain to form a 6-8 membered ring, where the alkyl are unsubstituted or substituted with 1-3 substituents where the substiuents are independently selected from: halo, hydroxy, —COR$^{11}$, C$_{1-3}$alkyl, and C$_{1-3}$alkoxy,
or R$^{16}$ and R$^{18}$ may be joined together by a —O—C$_{1-2}$ alkyl-O-chain to form a 6-7 membered ring, where the alkyl are unsubstituted or substituted with 1-3 substituents where the substiuents are independently selected from: halo, hydroxy, —COR$^{11}$, C$_{1-3}$alkyl, and C$_{1-3}$alkoxy;

R$^{19}$ is selected from:
(a) hydrogen,
(b) phenyl,
(c) C$_{1-6}$alkyl which may be substituted or unsubstituted with 1-6 of the following substituents: —COR$^{11}$, hydroxy, fluoro, chloro, —O—C$_{1-3}$alkyl; or R$^2$ and R$^{19}$ can also be joined together to form a heterocycle ring with a linker selected from the following list (with the left side of the linker being bonded to the amide nitrogen at R$^{19}$):
(a) —CH$_2$(CR$^{28}$R$^{28}$)$_{1-3}$—,
(b) —CH$_2$NR$^{29}$—
(c) —NR$^{29}$CR$^{28}$R$^{28}$—,
(d) —CH$_2$O—,
(e) —CH$_2$SO$_2$—,
(f) —CH$_2$SO—,
(g) —CH$_2$S—,
(h) —CR$^{28}$R$^{28}$—,
where R$^{28}$ is selected from selected from:
(a) hydrogen,
(b) hydroxy,
(c) halo,
(d) C$_{1-3}$alkyl, where the alkyl is unsubstituted or substituted with 1-6 substituents independently selected from: fluoro, and hydroxy,
(e) —NR$^{12}$R$^{12}$,
(f) —COR$^{11}$,
(g) —CONR$^{12}$R$^{12}$,
(h) —NR$^{12}$COR$^{13}$,
(i) —OCONR$^{12}$R$^{12}$,
(j) —NR$^{12}$CONR$^{12}$R$^{12}$,
(k) -heterocycle,
(l) —CN,
(m) —NR$^{12}$—SO$_2$—NR$^{12}$R$^{12}$,
(n) —NR$^{12}$—SO$_2$—R$^{14}$,
(o) —SO$_2$—NR$^{12}$R$^{12}$, and
(p) =O, where R$^{28}$ is connected to the ring via a double bond (in which case the other R$^{28}$ at the same position is nothing, and
where R$^{29}$ is selected from:
(a) hydrogen,
(b) C$_{1-3}$alkyl, where the alkyl is unsubstituted or substituted with 1-6 substituents independently selected from: fluoro, and hydroxy,
(c) COR$^{13}$,
(d) SO$_2$R$^4$, and
(e) SO$_2$NR$^{12}$R$^{12}$;

$R^{25}$ and $R^{26}$ are independently selected from:
- (a) =O, where $R^{25}$ and/or $R^{26}$ is oxygen and is connected via a double bond.
- (b) hydrogen,
- (c) phenyl,
- (d) $C_{1-6}$alkyl which may be substituted or unsubstituted with 1-6 of the following substituents: —$COR^{11}$, hydroxy, fluoro, chloro, —O—$C_{1-3}$alkyl;

m is selected from 0, 1, or 2;
n is selected from 1 or 2;
the dashed line represents a single or a double bond;

and pharmaceutically acceptable salts thereof and individual diastereomers thereof.

A further embodiment of the present invention includes compounds of formula Ia.

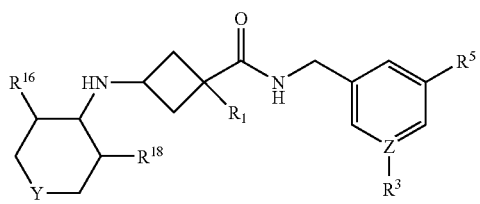

Ia wherein $R^1$, $R^3$, $R^5$, $R^{16}$, $R^{17}$, Y, and Z are defined above, and pharmaceutically acceptable salts and individual diastereomers thereof.

A still further embodiment of the present invention include compounds of formula IIa:

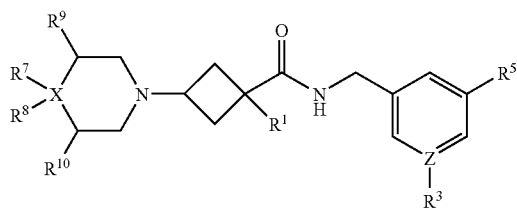

IIa

Wherein $R^1$, $R^5$, $R^7$, $R^8$, $R^9$, $R^{10}$ X and Z are described above.

A further embodiment of the present invention includes compounds of formula IIb.

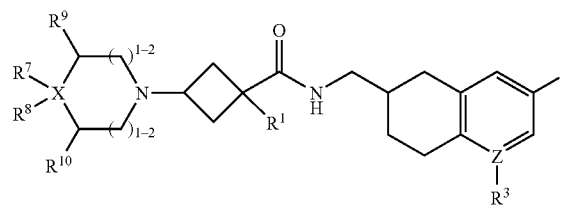

IIb wherein $R^1$, $R^3$, $R^5$, $R^7$, $R^8$, $R^9$, $R^{10}$, X, and Z are defined above, and pharmaceutically acceptable salts and individual diastereomers thereof.

A still further embodiment of the present invention includes compounds of formula IIc:

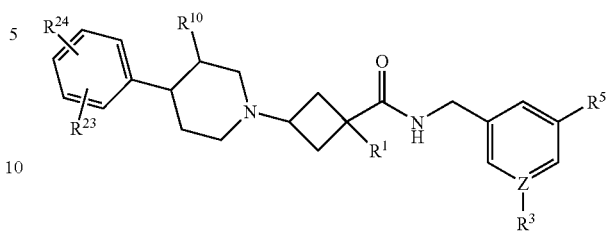

IIc

Wherein $R^1$, $R^3$, $R^5$, $R^{10}$, and Z are described above, and $R^{23}$ and $R^{24}$ are independently selected from:
- (a) hydrogen,
- (b) halo,
- (c) trifluoromethyl,
- (d) hydroxy,
- (e) $C_{1-3}$alkyl,
- (f) —O—$C_{1-3}$alkyl,
- (g) —$C_{0-3}$—$CO_2H$,
- (h) —$C_{0-3}$—$CO_2C_{1-3}$alkyl,
- (i) —CN, and
- (j) —$C_{0-3}$-heterocycle,
- or where the R23 and R24 are joined together to form a heterocycle which is fused to the phenyl ring, and which itself may be unsubstituted or substituted with 1-2 substituents independently selected from hydroxy, halo, —COR11, and —$C_{1-3}$alkyl;

and pharmaceutically acceptable salts and individual diastereomers thereof.

Another embodiment of the present invention includes compounds of formula IId:

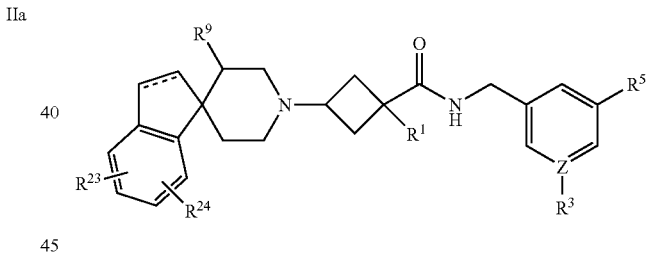

IId wherein $R^1$, $R^3$, $R^5$, $R^9$, $R^{23}$, $R^{24}$, and Z are defined above and the dashed line represents a single or a double bond, and pharmaceutically acceptable salts and individual diastereomers thereof.

Another embodiment of the present invention includes compounds of formula IIe:

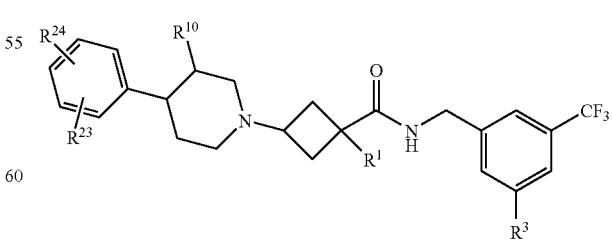

IIe

Wherein $R^1$, $R^3$, $R^5$, $R^{10}$, $R^{23}$, and $R^{24}$ are described above, and pharmaceutically acceptable salts and individual diastereomers thereof.

A still further embodiment of the present invention includes those of formula IIf:

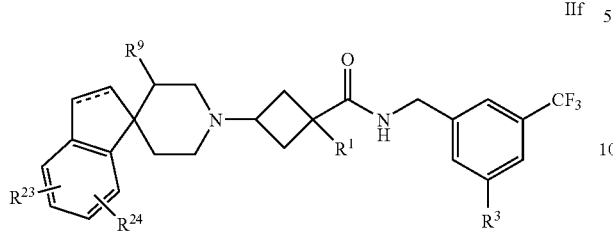

wherein $R^1$, $R^3$, $R^5$, $R^9$, $R^{23}$, and $R^{24}$ are defined above, and pharmaceutically acceptable salts and individual diastereomers thereof.

In a still further aspect of the present invention X is C, O or N.

In a still further aspect of the present invention X is C.

In a still further aspect of the present invention Y is —CH$_2$— or —O—.

In a further aspect of the present invention Z is C.

In another aspect of the present invention $R^1$ is selected from:
hydrogen, phenyl, heterocycle, —C$_{1-6}$alkyl, —C$_{0-6}$alkyl-O—C$_{1-6}$alkyl, and
—(C$_{0-6}$alkyl)-(C$_{3-7}$cycloalkyl)-(C$_{0-6}$alkyl),
where the alkyl, phenyl, heterocycle, and the cycloalkyl are unsubstituted or substituted with 1-7 substituents where the substituents are independently selected from:
(a) halo,
(b) hydroxy,
(c) —O—C$_{1-3}$alkyl,
(d) trifluoromethyl,
(f) C$_{1-3}$alkyl,
(g) —O—C$_{1-3}$alkyl,
(h) —COR$^{11}$,
(i) —CN,
(j) —NR$^{12}$R$^{12}$, and
(k) —CONR$^{12}$R$^{12}$.

In a still further aspect of the present invention $R^1$ is selected from:
(1) —C$_{1-6}$alkyl, which is unsubstituted or substituted with 1-6 substituents where the substituents are independently selected from:
(a) halo,
(b) hydroxy,
(c) —O—C$_{1-3}$alkyl,
(d) trifluoromethyl, and
(e) —COR$^{11}$,
(2) —C$_{0-6}$alkyl-O—C$_{1-6}$alkyl-, which is unsubstituted or substituted with 1-6 substituents where the substituents are independently selected from:
(a) halo,
(b) trifluoromethyl, and
(c) —COR$^{11}$,
(3) —(C$_{3-5}$cycloalkyl)-(C$_{0-6}$alkyl), which is unsubstituted or substituted with 1-7 substituents where the substituents are independently selected from:
(a) halo,
(b) hydroxy,
(c) —O—C$_{1-3}$alkyl,
(d) trifluoromethyl, and
(e) —COR$^{11}$,
(4) phenyl or heterocycle which is unsubstituted or substituted with 1-3 substituents where the substituents are independently selected from:
(a) halo,
(b) hydroxy,
(c) —O—C$_{1-3}$alkyl,
(d) trifluoromethyl, and
(e) —COR$^{11}$, In a further aspect of the present invention $R^1$ is selected from:
(a) hydrogen,
(b) C$_{1-6}$alkyl, which may be unsubstituted or substituted with 1-6 substituents independently selected from: fluoro and hydroxy
(c) phenyl, and
(d) pyridyl.

In a still further aspect of the present invention that $R^1$ is selected from:
(a) hydrogen
(b) —CH(CH$_3$)$_2$,
(c) —C(OH)(CH$_3$)$_2$.
(b) —CH(OH)CH$_3$,
(c) —CH$_2$CF$_3$,
(d) —CH$_3$, and
(e) phenyl, In another aspect of the present invention $R^2$ is hydrogen.

In still another aspect of the present invention when Z is N, $R^3$ is nothing.

In a still further aspect of the present invention when Z is C, $R^3$ is selected from:
(a) hydrogen
(b) halo
(c) hydroxy
(d) C$_{1-3}$alkyl, where the alkyl is unsubstituted or substituted with 1-6 substituents independently selected from: fluoro, and hydroxy,
(e) —COR$^{11}$,
(f) —CONR$^{12}$R$^{12}$,
(g) -heterocycle,
(h) —NR$^{12}$—SO$_2$—NR$^{12}$R$^{12}$,
(i) —NR$^{12}$—SO$_2$-R$^{14}$,
(j) —SO$_2$—NR$^{12}$R$^{12}$,
(k) -nitro, and
(l) —NR12R12;

In another aspect of the present invention, when Z is C, $R^3$ is selected from:
(a) fluoro,
(b) trifluoromethyl,
(c) hydrogen;

In a still further aspect of the present invention $R^4$ is hydrogen.

In another aspect of the present invention $R^5$ is selected from:
(a) C$_{1-6}$alkyl substituted with 1-6 fluoro,
(b) —O—C$_{1-6}$alkyl substituted with 1-6 fluoro,
(c) chloro,
(d) bromo, and
(e) phenyl.

In a still further aspect of the present invention $R^5$ is selected from:
(a) trifluoromethyl,
(b) trifluoromethoxy,
(c) chloro,
(d) bromo, and
(e) phenyl.

In a still further aspect of the present invention $R^5$ is trifluoromethyl.

In another aspect of the present invention $R^6$ is hydrogen.

In another aspect of the present invention $R^7$ is phenyl, heterocycle, $C_{3-7}$cycloalkyl, $C_{1-6}$alkyl, —$COR^{11}$, and —CONH—V—$COR^{11}$, where V is selected from $C_{1-6}$alkyl or phenyl, and where the phenyl, heterocycle, $C_{3-7}$cycloalkyl, and $C_{1-6}$alkyl is unsubstituted or substituted with 1-5 substituents where the substituents are independently selected from:
(a) halo,
(b) trifluoromethyl,
(c) hydroxy,
(d) $C_{1-3}$alkyl,
(e) —O—$C_{1-3}$alkyl,
(f) —$COR^{11}$,
(g) —CN,
(h) -heterocycle, and
(i) —$CONR^{12}R^{12}$.

In an additional aspect of the present invention (when X is not O) $R^7$ is phenyl, heterocycle, $C_{1-4}$alkyl, —$COR^{11}$, and —CONH—V—$COR^{11}$;

V is selected from $C_{1-6}$alkyl or phenyl; and the phenyl, heterocycle, and $C_{1-4}$alkyl is unsubstituted or substituted with 1-3 substituents where the substituents are independently selected from:
(a) halo,
(b) hydroxy,
(c) $C_{1-3}$alkyl,
(d) —O—$C_{1-3}$alkyl,
(e) —$COR^{11}$, and
(f) -heterocycle.

In another aspect of the present invention when X is O, $R^8$ is nothing;

In another aspect of the present invention X is C, $R^8$ is hydrogen;

In another aspect of the present invention $R^9$ is hydrogen;

In another aspect of the present invention $R^{10}$ is selected from:
(a) hydrogen,
(b) hydroxy,
(c) —$CH_3$,
(d) —O—$CH_3$, and
(e) =O (where $R^9$ is joined to the ring via a double bond).

In still another aspect of the present invention $R^{15}$ is hydrogen or methyl.

In another aspect of the present invention $R^{16}$ is selected from:
(a) hydrogen,
(b) $C_{1-3}$alkyl, which is unsubstituted or substituted with 1-6 fluoro,
(c) —O—$C_{1-3}$alkyl, and
(d) fluoro, and
(e) hydroxy.

In yet another aspect of the present invention $R^{16}$ is selected from:
(a) hydrogen,
(d) trifluoromethyl,
(c) methyl,
(d) methoxy,
(e) ethoxy,
(f) ethyl,
(g) fluoro, and
(h) hydroxy.

In another aspect of the present invention $R^{17}$ is hydrogen.

In another aspect of the present invention $R^{18}$ is selected from:
(a) hydrogen,
(b) methyl, and
(c) methoxy.

In still another aspect of the present invention $R^{18}$ is hydrogen.

In yet another aspect of the present invention $R^{16}$ and $R^{18}$ are joined together by a —$CH_2CH_2$— chain or a —$CH_2CH_2CH_2$— chain to form a cyclopentyl ring or a cyclohexyl ring.

In still another aspect of the present invention $R^{25}$ is hydrogen.

In another aspect of the present invention $R^{26}$ is oxygen and connected via a double bond.

In still another aspect of the present invention l=1.

In still another aspect of the present invention m=1.

In yet another aspect of the present invention n=1.

Representative compounds of the present invention include those presented in the Examples and pharmaceutically acceptable salts and individual diastereomers thereof.

The compounds of the instant invention have at least two asymmetric centers at the 1- and 3-positions of the cyclobutyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of selected compounds of this orientation, with substituents on the cyclopentyl ring (amide and amine units), are as depicted below:

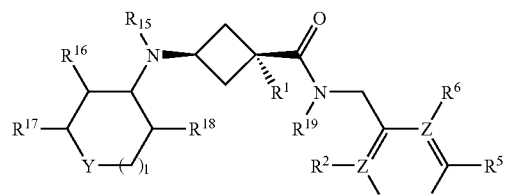

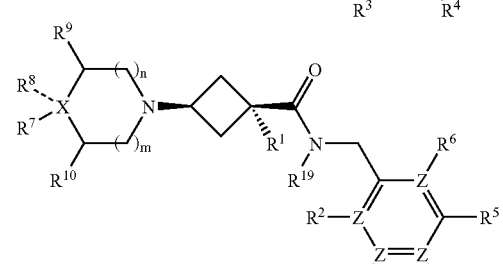

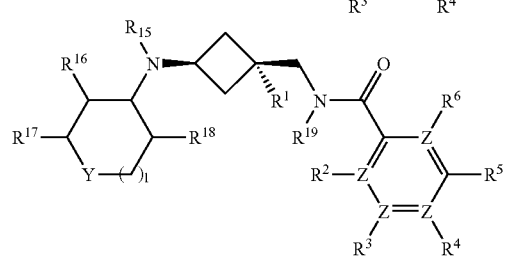

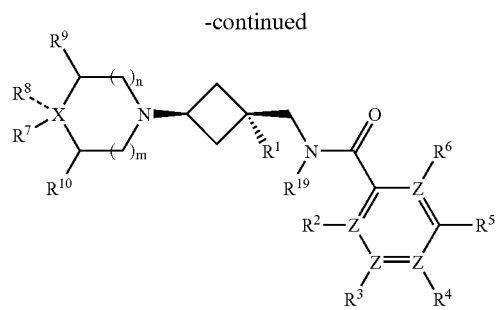

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Several methods for preparing the compounds of this invention are illustrated in the following Schemes and Examples. Starting materials are made by known procedures or as illustrated.

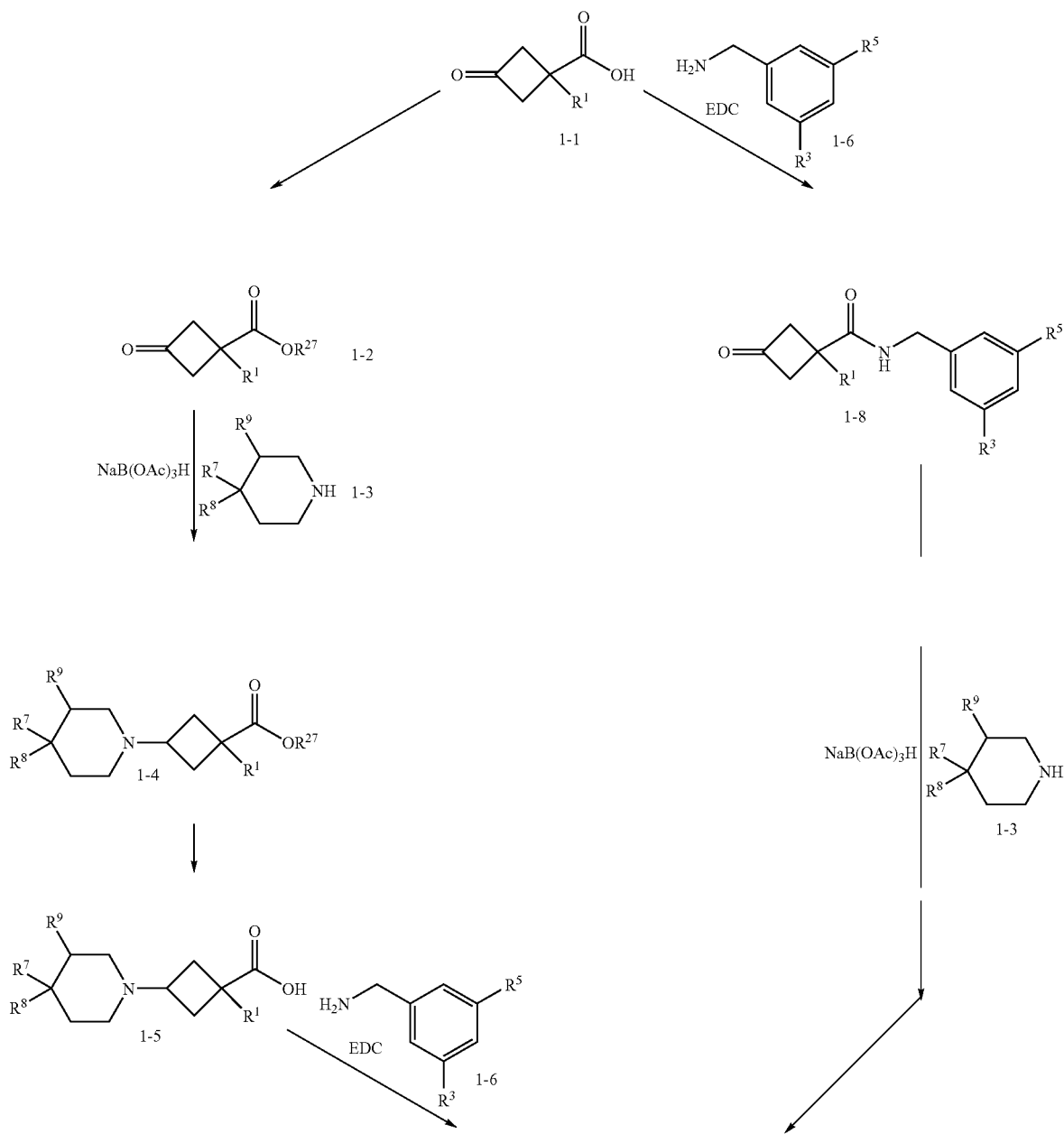

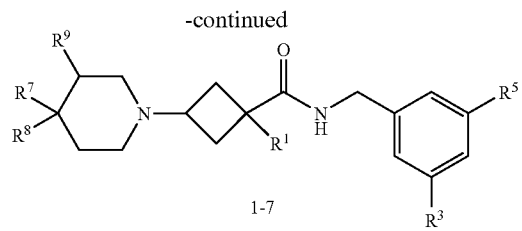

The preparation of compounds within the scope of the instant invention which bear a 1,1,3-trisubstituted cyclobutane framework is detailed in Scheme 1. Keto-acid 1-1 (the preparation of which is described in Scheme 2) can first be protected as the corresponding ester, where $R^{27}$ represents an alkyl such as methyl, ethyl, tert-butyl or benzyl which serves as a protecting group (Greene, T; Wuts, P. G. M. *Protective Groups in Organic Synthesis*, John Wiley & Sons, Inc., New York, N.Y. 1991). Reductive amination of 1-2 with an amine preferably of the from 1-3 (a preparation of which is depicted in Scheme 3) in the presence of a reducing agent such as sodium cyanoborhydride or sodium triacetoxyborohydride gives amino-ester 1-4. Conversion of ester 1-4 to the carboxylic acid 1-5 can be achieved by a number of conditions depending on the nature of the ester. For example, methyl or ethyl esters can be readily saponified with sodium hydroxide, or lithium hydroxide; tert-butyl ester can be removed by treatment with TFA. Coupling of the acid 1-5 with amine 1-6 (a preparation of which is described in Scheme 4), to give chemokine modulators of the form 1-7, can be accomplished by the standard amide bond formation conditions using a coupling reagent such as DCC, EDC and a catalyst such as DMAP, HOBT or HOAT. Alternativly 1-1 can be directly coupled to amine 1-6 to give the keto-amide 1-8. Reductive amination with amine 1-3 in the presence of a borohydride such as sodium triacetoxyborohydride or sodium cyanoborohydride then provides the chemokine modulator 1-7.

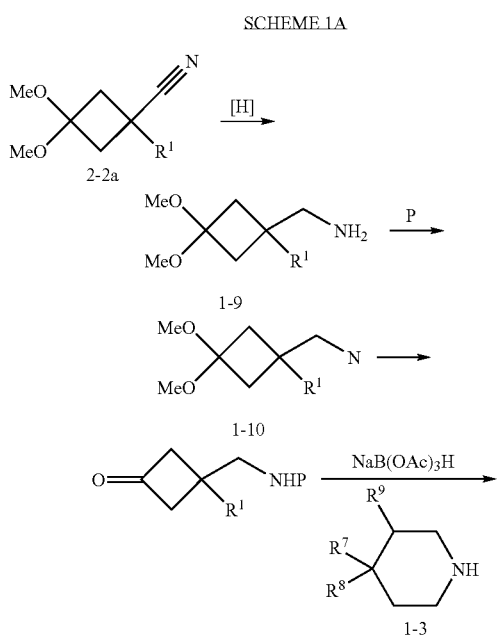

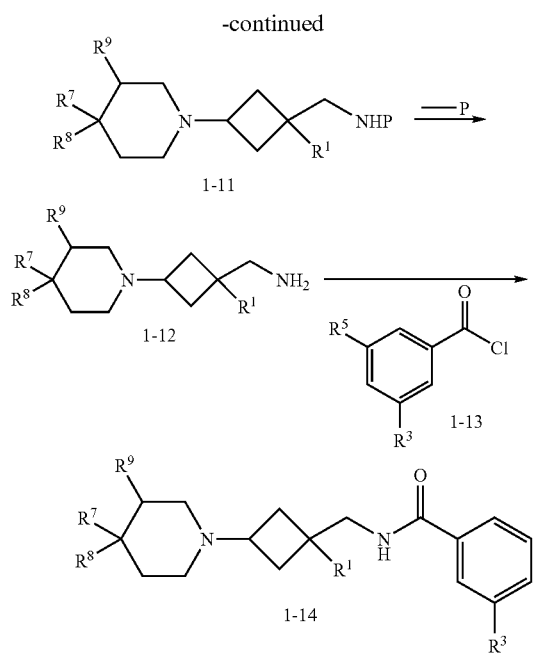

Scheme 1A depicts the preparation of chemokine modulators of the form 1-14. Intermediate 2-2a (described in Scheme 2) is first reduced to the primary amine 1-9 by catalytic hydrogenation using Raney nickel. Protection of the amine with the appropriate protecting group, such as a tert-butylcarbamate, by treatment with di-tert-butyl dicarbonate followed by reductive amination with amine 1-3 gives intermediate 1-11. Removal of the protecting group, with for example HCl in dioxane or TFA for the boc protected amine gives the free amine 1-12. Acylation of the amine with an acid chloride (1-13) gives the chemokine modulator 1-14. Alternatively the amine can be coupled (as described in Scheme 1) to an appropriate benzoic acid (not shown) to give similar amides 1-14.

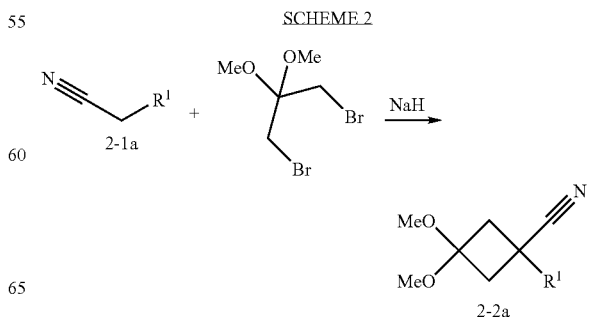

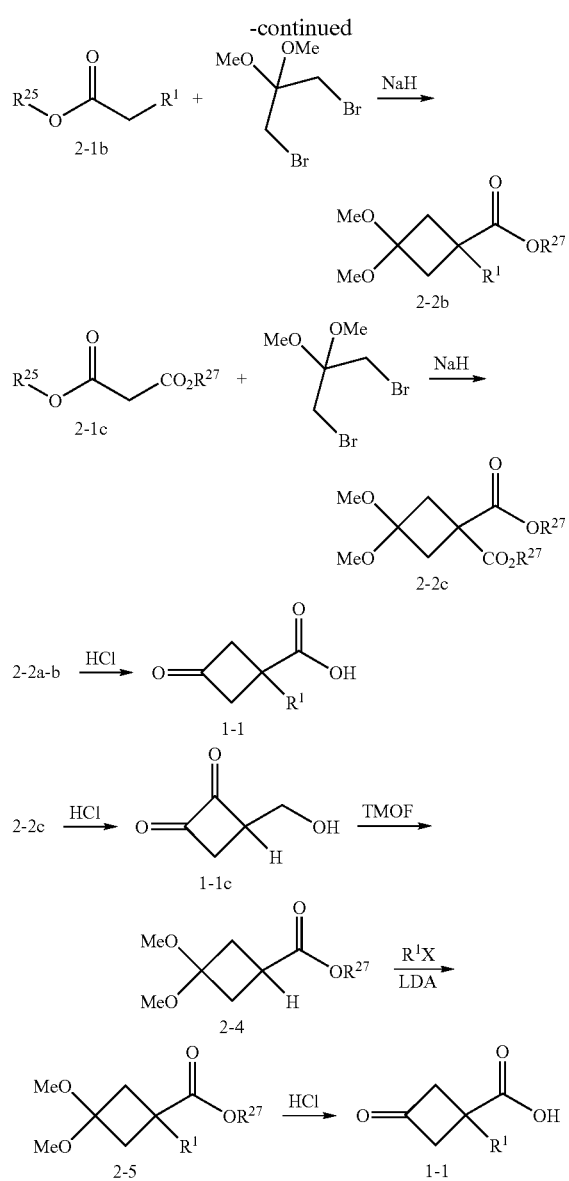

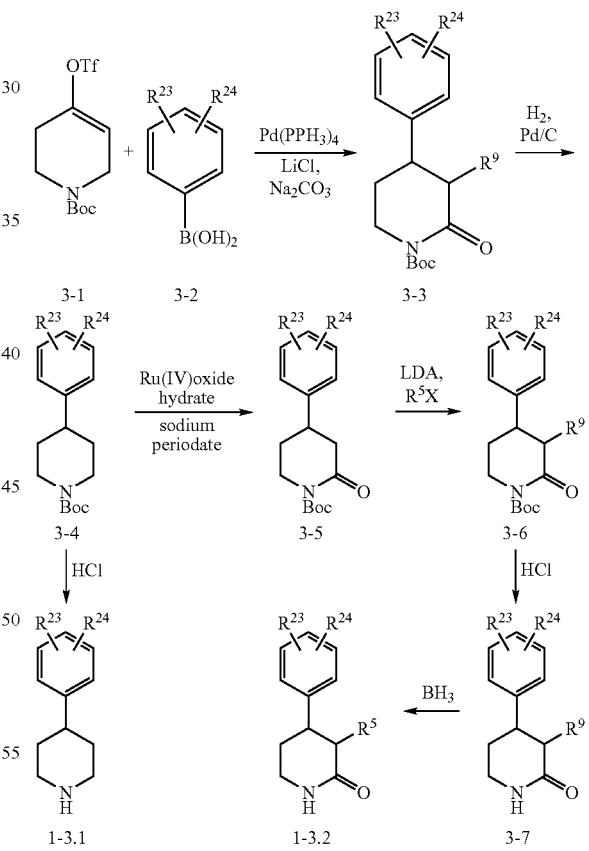

Amines 1-3 were obtained from various sources. Some were commercially available, some were known from the literature and could be prepared according to published procedures, and some were prepared as described herein. Since their structures and the methods for their preparation are diverse, only one Scheme will be outlined in this section; individual syntheses of amines 1-3 can be found in the Experimental Section. Scheme 3 shows one method for the synthesis of 4-aryl substituted piperidines as well as 4aryl-3-alkyl-piperidines. Enol triflate 3-1 (prepared according to Wustrow, D. J., Wise, L. D., *Synthesis*, (1991), 993-995.) could be coupled to boronic acids 3-2 as described by Wustrow and Wise. Hydrogenation of the olefin in 4-3 could be achieved using hydrogen in the presence of a catalyst such as Pd(OH)$_2$/C. Oxidation of 3-4 using Ru(IV)oxide hydrate and sodium periodate leads to Boc-lactam 3-5. Alkylation with an alkyl halide in the presence of a base such as LDA gives 3-6, with the trans product being predominant. Removal of the Boc protecting group could be achieved using standard acidic conditions, such as HCl in dioxane or TFA/DCM. Reduction of the lactam 3-7 with, for example borane provides 1-3.2. Alternatively, intermediate 3-4 can itself be deprotected under acidic conditions to afford piperidine 1-3.1.

As depicted in Scheme 2, the keto cyclobutanoic acid (1-1) can be readily synthesized from commercially available materials. The initial protected intermediates of the form 2-2 can be made by a double alkylation reaction of an active ester (2-1b) or nitrile (2-1a) with 1,3-dibromo 2,2-dimethoxypropane, using a base such as sodium hydride. Removal of the dimethyl acetal and the hydrolysis of the ester or nitrile can be accomplished under acidic conditions in one reaction step to give intermediate 1-1. In the case where $R^1$ is an ester functionality (2-1c) this hydrolysis is accompanied by decarboxylation to give the simple ($R^1$=H) keto-cyclobutane (1-1c). The ketone (1-1c) can be reprotected as the dimethyl acetal using trimethyl orthoformate with an acid catalyst in an appropriate solvent. When this solvent is methanol, the reaction is accompanied by esterification of the carboxylic acid to give 2-4 (where $R^{27}$ is a methyl group). Alkylation of 2-4 with an alkyl halide or an aldehyde or ketone (to give an appropriate aldol product) gives intermediates 2-5. The deprotection of the ketone and hydrolysis of the ester can again be achieved in one step under acidic conditions to give 1-1.

Amines of the form 1-6 are synthesized in a variety of ways. An example of such a synthesis is depicted in Scheme 4. According to this, the commercially available 3-trifluoromethyl-5-amino bromobenzene (4-1) is converted to the corresponding nitrile using zinc cyanide in the presence of palladium, and a Sandmeyer reaction is then used to produce the respective halide 6-3, $R^3$=Cl, I. The reduction of the nitrile in the presence of an aromatic halide to the corresponding amine can be successfully accomplished e.g. with borane in THF.

SCHEME 4

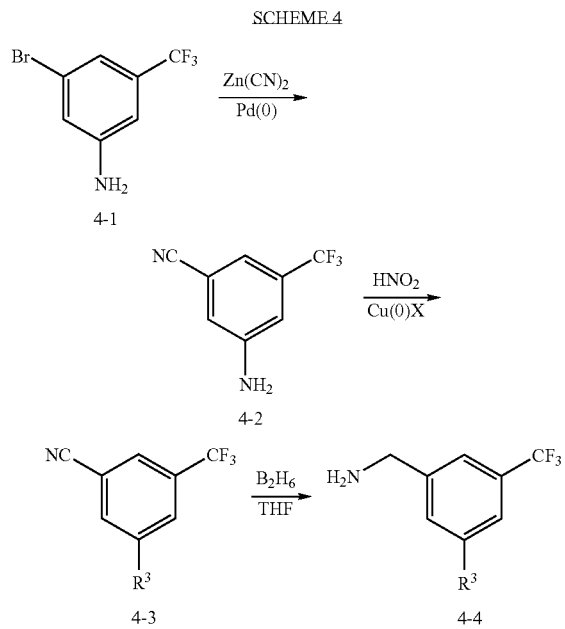

Another example, which describes a synthesis of a pyridyl-methylamine is detailed in Scheme 5. According to this, the commercially available 5-trifluoromethyl-2-pyridinal (5-1) is brominated in acetic acid and the aromatic bromide is converted to the respective aldehyde 5-3 by transmetalation and quench with dimethyl formamide. Dehydration of the corresponding oxime yields the required nitrile (5-4) and then phosphoryl chloride is used to produce the respective aromatic chloride. The simultaneous reduction of the nitrile and chloride to yield 5-6 can be accomplished with catalytic hydrogenation, preferably with Raney nickel and elevated pressure.

SCHEME 5

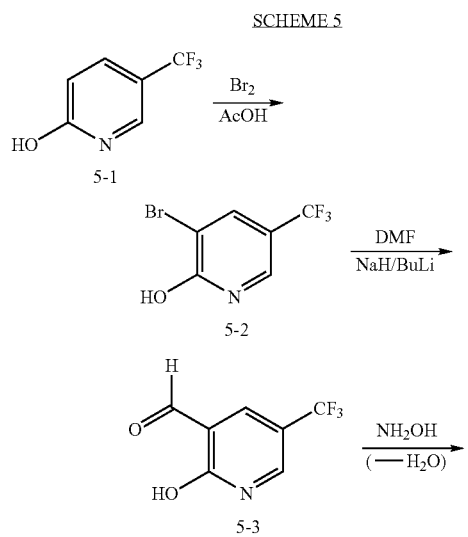

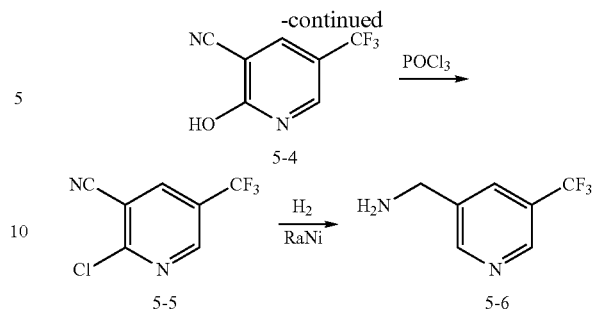

Additional examples of benzyl amines incorporated into the amide portion of compounds within the scope of the instant invention, as well as their syntheses are further described in the Experimental section.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

INTERMEDIATE 1

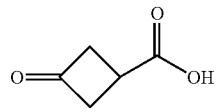

Step A

To a flame-dried three-necked round-bottomed flask equipped with a stir-bar, addition funnel, thermometer, and reflux condenser, was suspended 60% NaH (8.4g, 210 mmol) in dry DMF under nitrogen. Diisopropylmalonate (36.3 ml, 191 mmol) was added dropwise while keeping temperature under 70° C. On cessation of gas evolution, 1,3-dibromo-2,2-dimethoxypropane (25g, 95 mmol) was added. The reaction mixture was stirred at 140° C. for 48 h before being cooled to room temperature and poured into an aqueous solution of NH$_4$Cl (25g in 400 mL) to prevent emulsion formation. The aqueous layer was extracted with hexanes (3×). The combined organic layers were washed with water and a saturated NaHCO$_3$ solution, dried over anhydrous MgSO$_4$, and concentrated in vacuo. The crude product was purified by vacuum distillation (0.1 mm, 92-100° C.) to yield pure product (12.0 g, 43.6%). 1H NMR (400 MHz, CDCl3) δ 5.07 (p, J=12.5 Hz, 6.25 Hz, 2H), 3.17 (s, 6H), 2.71 (s, 4H), 1.25 (d, J=6.2 Hz, 12H).

Step B

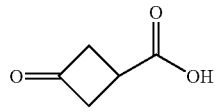

Product from Step A (4.8 g, 17 mmol) was stirred with 20% HCl (20 ml) at reflux for 60 h before being cooled to room temperature. Ether was added and the solution was vigorously stirred for 24 hours. The ether layer was removed and the aqueous layer was extracted with ether (3×). The combined organic layers were dried over anhydrous MgSO₄ and concentrated in vacuo to yield Intermediate 1 (1.84 g, 96.8%). The crude product was used on next step. NMR (400 MHz, CDCl3) δ 3.52-3.26 (m, 5H).

INTERMEDIATE 2

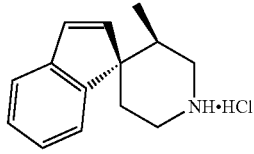

Step A

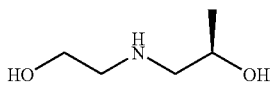

To a cooled (0° C.) solution of ethanolamine (41.8 g, 0.685 mol) in water (90 mL) was added neat (R)-propylene oxide (4.97 g, 85.6 mmol), dropwise. After 1 h at 0° C. the reaction was allowed to rise to room temperature and stirred overnight. The reaction mixture was concentrated at ~80° C. in vacuo to remove the water and most of the ethanolamine, to give 11.79 g of crude product, containing some residual ethanolamine. This material was used without further purification in Step B.

Step B

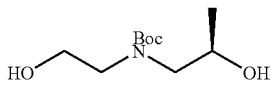

The diol prepared in Step A (11.8 g crude [~86% pure], ca. 83 mmol) was dissolved in DCM (150 mL) and treated with di-tert-butyl dicarbonate (23.4 g, 107 mmol) in DCM (75 mL) over 15 min. The reaction mixture was stirred over the weekend, concentrated, and purified by MPLC, eluting with 5% MeOH/EtOAc to provide 14.8 g (81%) of product.

Step C

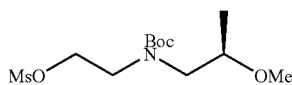

To a solution of the Boc-protected diol prepared in Step B (13.2 g, 60.3 mmol) and triethylamine (21.0 mL, 15.3 g, 151 mmol) in DCM (150 mL) at 0° C. was added dropwise methanesulfonyl chloride (9.56 mL, 14.1 g, 125 mmol). The reaction mixture was then stirred for 1.5 h, diluted with more DCM (100 mL) and washed with 3N HCl (250 mL). The aqueous layer was extracted again with DCM (200 mL), and the organic layers were combined and washed with 1N HCl (250 mL), saturated NaHCO₃ solution (250 mL), and brine (250 mL). The organic layer was dried over MgSO₄, filtered, and concentrated to give 22.8 g of crude bis-mesylate, which was used immediately. If not used immediately the bis-mesylate underwent decomposition.

Step D

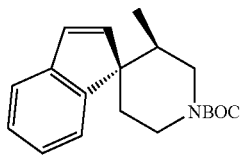

Indene (7.03 mL, 7.00 g, 60.3 mmol) was added dropwise over 4 min to a 1.0 M THF solution of LHMDS (127 mL, 127 mmol) at 0° C. After stirring for an additional 30 min., this solution was transferred via cannula to a solution of bis-mesylate (22.6 g, 60.3 mmol), prepared as described in Step C above, in THF (75 mL) at 0° C. The mixture was stirred for 2 h, warmed to rt and stirred overnight. The reaction mixture was partially concentrated and then partitioned between ethyl acetate and water. The aqueous layer was extracted again with ethyl acetate and the organic layers were combined. The organic phase was then washed with brine, dried over MgSO₄, filtered and concentrated to give 17.3 g of crude product. Purification by MPLC, eluting with 15% ethyl acetate/hexane, afforded 9.51 g (53%) of piperidine as a ~3:1 mixture of trans to cis (determined by H NMR). The mixture was crystallized from hot hexane to give 6 g (33%) of pure trans isomer (>20:1 by H NMR). H NMR (CDCl₃, 400 MHz): □ 7.29 (dt, J=6.4, 1.6 Hz, 1H), 7.20 (m, 3H), 6.83 (d, J=6.0 Hz, 1H), 6.67 (d, J=5.6 Hz, 1H), 4.20 (br s, 2H), 2.97 (br t, J=3.2 Hz, 1H), 2.69 (br t, J=2.4 Hz, 1H), 2.16 (m, 1H), 2.07 (dt, J=4.4, 13.2 Hz, 1H), 1.49 (s, 9H), 1.25 (m, 1H), 0.31 (d, J=6.8 Hz, 3H).

Step E

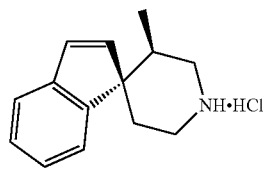

The Boc-piperidine prepared in Step D (4.35 g, 14.5 mmol) was dissolved in an anhydrous 4 N HCl solution in dioxane and stirred at rt for 1 h. The reaction mixture was then concentrated to afford 3.81 g of product. EI-MS calc. for C14H17N: 199; Found: 200 (M)⁺.

INTERMEDIATE 3

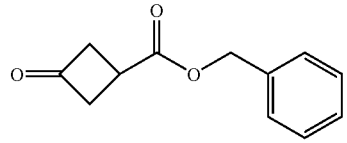

Intermediate 1 (3.5 g, 30.7 mmol), benzyl alcohol (3.17 ml, 30.7 mmol), DMAP (375 mg, 3.07 mmol), EDC (8.8 g, 46.0 mmol) and DCM (100 ml) were mixed together and stirred at room temperature for 18 hours. The reaction mixture was washed with water (3×). The combined aqueous layer was extracted with DCM. The combined organic layer was washed with brine, dried over anhydrous MgSO₄, and concentrated in vacuo. Crude product was purified by MPLC (30:70, ethyl acetate:hexanes) to yield Intermediate 3 (5.25 g, 84.0%). NMR (400 MHz, CDCl3) δ 7.39 (m, 4H), 5.21 (s, 2H), 3.49-3.41 (m, 2H), 3.36-3.28 (m, 3H).

INTERMEDIATE 4

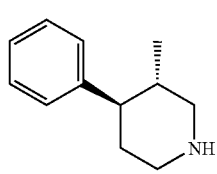

Step A

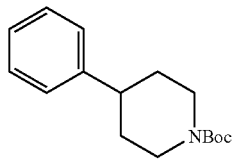

A solution of 4-phenylpiperidine hydrochloride (7.00 g, 35.8 mmol), di-tert-butyl dicarbonate (11.7 g, 53.6 mmol), DIEA (6.2 mL, 35.8 mmol) and DCM (125 mL) was stirred at room temperature and the reaction was monitored by HPLC. Upon completion of reaction, the reaction mixture was concentrated in vacuo and redissolved in EtOAc. Insoluble DIEA hydrochloride was filtered out. The filtrate was concentrated to dryness and redissolved in DCM, washed with 15% citric acid, saturated NaHCO₃ and brine, dried over anhydrous MgSO₄, and concentrated in vacuo. The crude product was purified by flash chromatography (10:90, EtOAc:hexanes) to yield 3-A (8.48 g, 90.6%). 1H NMR (400 MHz, CDCl3) δ 7.35-7.30 (m, 2H), 7.25-7.21 (m, 3H), 4.26 (s, 2H), 2.82 (t, J=12 Hz, 2H), 2.66 (tt, J=12.1 Hz, 3.5 Hz, 1H), 1.84 (d, J=13.2 Hz, 2H), 1.63 (dq, J=12.7 Hz, 4.1 Hz, 2H), 1.52 (d, J=17.4 Hz, 9H).

Step B

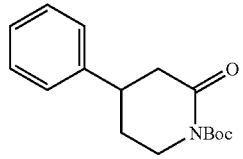

The product from Step A (2.10 g, 8.0 mmol) and RuO₂ (0.30 g) were suspended in CHCl₃ (150 mL) which had been de-alcoholed by washing with water (3×) (Solution A). In a separate flask, NaIO₄ (6.8 g, 32 mmol) was suspended in water (150 mL) (Solution B). Solution B was added to Solution A and the combined mixture was vigorously stirred at room temperature for 2 days. The organic layer was separated and the aqueous layer was extracted with CHCl₃ (3×) and DCM (3×). MeOH (20 mL) was added to the combined organic layer to destroy excess oxidant. The mixture was filtered through celite. The filtrate was washed with 10% aqueous sodium thiosulfate (20 mL), dried over anhydrous MgSO₄, and concentrated in vacuo. The crude product was purified by MPLC (20:80, EtOAc:hexanes) to yield pure 3-B (867 mg, 39.4%). 1H NMR (500 MHz, CDCl3) δ 7.36 (app t, J=7.5 Hz, 2H), 7.29-7.27 (m, 1H), 7.23 (app d, J=7.3 Hz, 2H), 3.89 (dt, J=13.0 Hz, 4.5Hz, 1H), 3.64 (ddd, J=19.7 Hz, 11 Hz, 4.1 Hz, 1H), 3.14 (ddd, J=15.8 Hz, 11.2 Hz, 4.8 Hz, 1H), 2.86 (ddd, J=17.1 Hz, 5.5 Hz, 2.0 Hz, 1H), 2.65 (dd, J=17.2 Hz, 11.3 Hz, 1H), 2.24-2.18 (m, 1H), 2.00 (dddd, J=24.7 Hz, 16.0 Hz, 11.0 Hz, 5.0 Hz, 1H), 1.56 (s, 9H).

Step C

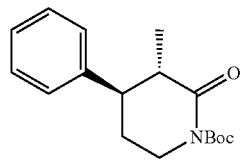

KHMDS (686 mg, 3.44 mmol) was dissolved in THF (10 ml) in a flamed dried flask under N₂. The mixture was cooled to −78° C. before a solution of the product from Step B (860 mg, 3.13 mmol) in THF (5 mL) was added slowly. The reaction mixture was stirred at −78° C. for 30 minutes before MeI (584 μL, 9.38 mmol) was added. The reaction was warmed up to room temperature slowly and stirred overnight. Saturated NH₄Cl was added and the solution was extracted with EtOAc (3×). Combined organic layer was dried over anhydrous MgSO₄ and concentrated in vacuo. The crude product was purified by MPLC (20:80, EtOAc:Hexanes) to yield 3-C (383 mg, 42.4%). 1H NMR (500 MHz, CDCl3) δ 7.35 (app t, J=7.4 Hz, 2H), 3.27 (m, 1H), 7.20 (app d, J=7.1 Hz, 2H), 3.86 (dt, J=12.8 Hz, 5.0 Hz, 1H), 3.74 (ddd, J=13.1 Hz, 10.1 Hz, 4.6 Hz, 1H), 2.69 (m, 2H), 2.14 (m, 1H), 2.05 (m, 1H), 1.57 (s, 9H), 1.10 (d, J=6.4 Hz, 3H).

Step D

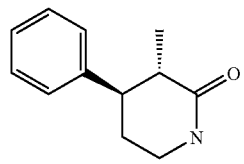

The product from Step C (1.34 g, 4.63 mmol) was stirred in 4 M HCl in dioxane (30 mL) for 2 hours before concentrated in vacuo to yield the desired HCl salt (871 mg, 99.4%). 1H NMR (400 MHz, CDCl3) δ 8.94 (s, 1H), 7.87 (s, 1H), 7.38 (m, 2H), 7.30 (m, 1H), 7.20 (m, 2H), 3.57 (m, 2H), 2.76-2.71 (m, 2H), 2.70-2.06 (m, 2H).

Step E

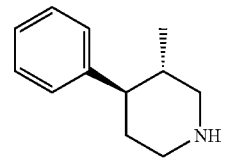

To a flamed-dried flask was added one pellet of LAH (1 g). Ether (20 mL) was added slowly to dissolve the LAH before the product from Step D (870 mg, 4.6 mmol) was added. The reaction mixture was stirred at room temperature overnight before cooled to 0° C. Water (1 mL) was added dropwise followed by a 15% NaOH solution (1 mL), and water (3 mL). The mixture was vigorously stirred for 3 hours before filtered and concentrated in vacuo. The product was redissolved in DCM and added 4N HCl to form a HCl salt of 3-E (805 mg, 82.7%). 1H NMR (400 MHz, CD3OD) δ 7.33 (m, 2H), 7.23 (m, 3H), 3.45 (m, 2H), 3.10 (m, 1H), 2.79 (t, J=6.8 Hz, 1H), 2.46 (m, 1H), 2.16-2.07 (m, 1H), 2.00-1.95 (m, 2H), 0.74 (d, J=6.4 Hz, 3H).

INTERMEDIATE 5

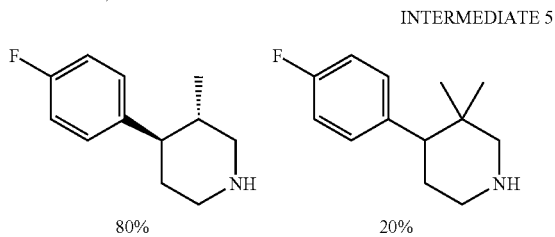

Intermediate 5 was synthesized from 4-fluoro4-phenylpiperidine using the reaction scheme detailed in the synthesis of Intermediate 4. A mixture of methyl and dimethyl compounds were synthesized.

INTERMEDIATE 6

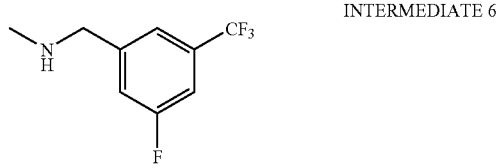

Step A

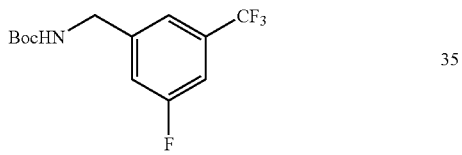

A solution of 3-fluoro-5-trifluoromethylbenzylamine (2 g, 10 mmol), di-tert-butyl-dicarbonate (3.4 g, 15 mmol), and DMAP (tare) in DCM (50 mL) was stirred at room temperature overnight. The reaction mixture was concentrated in vacuo, redissolved in EtOAc, washed with saturated NaHCO₃ and brine, dried over anhydrous MgSO₄. The crude product was purified by MPLC (15:85, EtOAc:hexanes) to yield 5-A (1.0 g, 33.3%).

Step B

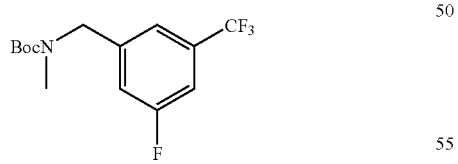

60% NaH (205 mg, 5.12 mmol) was suspended in DMF (25 mL) under nitrogen. The mixture was cooled to −78° C. before the product from Step A (1.0 g, 3.4 mmol) and MeI (640 μL, 10.2 mmol) were added. The solution was stirred at −78° C. for another 30 minutes before being raised to room temperature. The reaction was diluted with ether, washed with water (3×), dried over anhydrous MgSO₄, and concentrated in vacuo. The crude product was purified by MPLC (10:90, EtOAc:hexanes) to yield the product (823 mg, 78.5%). 1H NMR (500 MHz, CDCl3) δ 7.30 (s, 1H), 7.25 (d, J=8.0 Hz, 1H), 7.14 (d, J=8 Hz, 1H), 4.47 (s, 2H), 2.88 (d, J=14.5 Hz, 3H), 1.49 (d, J=10.3 Hz, 9H).

Step C

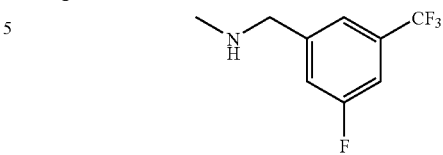

The product from Step B (823 mg, 2.68 mmol) was dissolved in 4 M HCl in dioxane (10 mL). Upon on completion of reaction, the solution was concentrated down to yield the desired product (614 mg, 94.3%). 1H NMR (400 MHz, CD3OD) δ 7.72 (s, 1H), 7.60 (t, J=4.5 Hz, 2H), 4.31 (s, 2H), 2.76 (s, 3H).

INTERMEDIATE 7

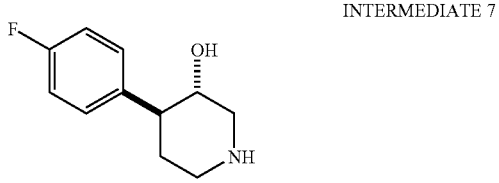

Step A

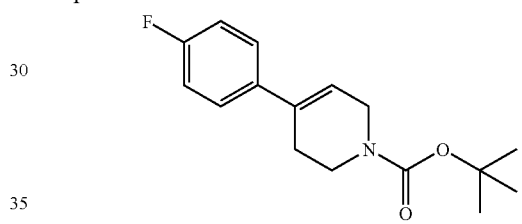

To a suspension of 4-(4-fluorophenyl)-1,2,3,6-tetrahydropyridine hydrochloride (10 g, 47 mmol) in dichloromethane (150 mL) was added diisopropylethylamine (8.97 mL, 51.5 mmol), followed by di-tert-butyl dicarbonate (12.27 g, 56.2 mmol), and the resulting mixture stirred at room temperature for 2 hours. N,N-dimethylethylenediamine (1 mL, 9 mmol) was added and stirring continued for a further 30 mins. The reaction mixture was washed with 5% citric acid solution (100 mL), water (2×100 mL), saturated NaCl (50 mL), dried over MgSO₄, filtered and concentrated in vacuo to give 13.5 g crude product, which was used without further purification in step B.

Step B

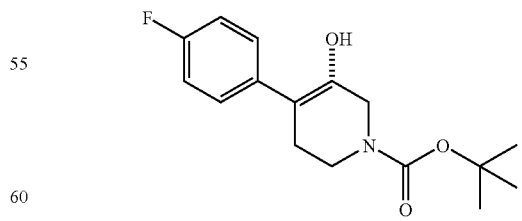

To a cooled (0° C.) solution of borane-methyl sulfide complex (5.9 mL, 59 mmol) in anhydrous tetrahydrofuran (100 mL) under an atmosphere of nitrogen, was added using a canula, a solution of the BOC tetrahydropyridine prepared in Step A (13.5 g, 49 mmol) in tetrahydrofuran (100 mL). The resulting mixture was stirred at room temperature for 17 hours, then cooled in an ice bath and sodium hydroxide (18 mL of a 3N solution, 53.8 mmol) added in a dropwise manner, followed by hydrogen peroxide (20 mL of a 30% solution). The resulting mixture was stirred at 45° C. for 1 hour, then poured into water (500 mL) and extracted with diethyl ether (3×100 mL). The combined diethyl ether layers were washed with water (500 mL), saturated $NaHCO_3$ (200 mL), saturated NaCl (150 mL), dried over $MgSO_4$, filtered and concentrated in vacuo to give 12.1 g (84%) of product. This material was used in Step C without further purification. H NMR ($CDCl_3$, 500 MHz): δ 7.26 (dd, J=5.5, 8.7 Hz, 2H), 7.03 (t, J=8.7 Hz, 2H), 4.40 (br m, 1H), 4.20 (br m, 1H), 3.64 (m, 1H), 2.76 (br m, 1H), 2.63 (br m, 1H), 2.53 (m, 1H), 1.86-1.64 (m, 3H), 1.48 (s, 9H).

Step C

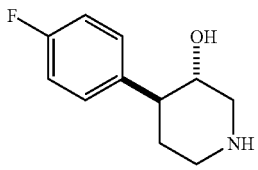

A solution of the BOC piperidine prepared in Step B (500 mg, 1.7 mmol) in methanol (20 mL) was saturated with anhydrous hydrogen chloride gas, and the resulting mixture left standing at room temperature for 7 hours. The mixture was concentrated in vacuo, and the residue partitioned between saturated $NaHCO_3$ (30 mL) and dichloromethane (20 mL). The organic layer was separated, and the aqueous layer extracted with further portions of dichloromethane (2×20 mL). The combined dichloromethane layers were dried over $MgSO_4$, filtered and concentrated in vacuo to give 260 mg (78%). ESI-MS calc. for $C_{11}H_{14}FNO$: 195; Found: 196 (M+H).

INTERMEDIATE 8

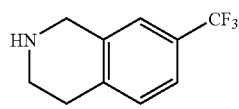

Step A

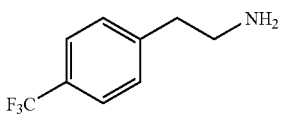

To a solution of 4-trifluoromethyl phenylacetonitrile (40 g, 215 mmol) in 2 N $NH_3$/MeOH (400 mL) was added Raney Ni (~4.0 g). The reaction mixture was placed in a Parr Apparatus and hydrogentated under 50 lb pressure of $H_2$ overnight. The solution was filtered through celite and concentrated in vacuo to yield the desired amine (38 g, 95%). ESI-MS calc. For $C_9H_{10}F_3N$: 189; Found: 190 (M+H).

Step B

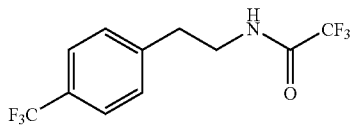

The above amine (Step A) (38 g, 200 mmol) and DIEA (52 mL, 300 mmol) were dissolved in DCM (300 mL). The solution was cooled to 0° C. before TFAA (36 mL, 250 mmol) was added slowly. The reaction mixture was stirred in the ice bath for another 10 minutes before being warmed up to room temperature. The reaction was completed in 30 minutes and was poured into water and extracted with DCM (2×). The organic layer was washed with 1 N HCl and saturated NaCl solution, dried over $MgSO_4$, and concentrated in vacuo to yield the desired amide (56 g, 98%). ESI-MS calc. For $C_{11}H_9F_6NO$: 285; Found: 286 (M+H).

Step C

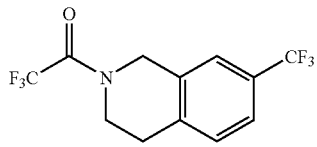

To a mixture of the amide (Step B) (73 g, 256 mmol) and paraformaldehyde (11.5 g, 385 mmol) was added 200 mL of acetic acid. The reaction mixture was stirred at room temperature for 5 min before concentrated sulfuric acid (200 mL). An exothermic reaction was observed. After 30 min, TLC showed a complete conversion. The mixture was cooled to RT before poured onto ice water (2000 mL) and extracted with EtOAc (3×500 mL). Combined organic layers were washed with water (2×), saturated $NaHCO_3$, and brine, dried over $MgSO_4$, filtered, evaporated and dried in vacuum. The desired amide (72.7 g, 96%) was obtained as a light-yellow solid. 1H NMR (400MHz, CDCl3) δ 7.22 (q, J=11.67 Hz, 8.46 Hz, 1H), 7.11 (t, J=10.53 Hz, 1H), 7.03 (d, J=11.67 Hz, 1H), 4.79 (d, J=23.57 Hz, 2H), 3.91 (t, J=6.18Hz, 1H), 3.87 (t, J=5.72 Hz, 1H), 2.97 (m, 2H).

ESI-MS calc. For $C_{12}H_9F_6NO$: 297; Found: 298 (M+H).

Step D

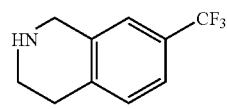

The amine (Step C) (50 g, 168 mmol) was dissolved in EtOH (200 mL) before solid $K_2CO_3$ (50 g, 360 mmol) and $H_2O$ (50 mL) were added. The reaction mixture was refluxed for 15 hours before concentrated in vacuo. The concentrate was diluted with $H_2O$ (100 mL) and extracted with DCM (5×). Combined organic layers were dried over $MgSO_4$, filtered, concentrated and purified on FC (10% [aq. NH4OH/MeOH 1/9]/DCM) to yield the amine (Step D)(30 g, 89%). 1H NMR (400 MHz, CDCl3) δ 7.11 (d, J=8.4 Hz, 1H), 7.01 (bd, J=8.4 Hz, 1H), 6.89 (s, 1H), 4.03 (s, 2H), 3.15 (t, J=6.1

Hz, 2H), 2.80 (t, J=5.6 Hz, 2H), 1.80 (s, 1H). ESI-MS calc. For C$_{10}$H$_{10}$F$_3$N: 201; Found: 202 (M+H).

INTERMEDIATE 9

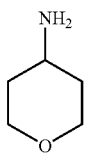

Step A

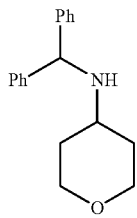

To a solution of tetrahydro-4H-pyran-4-one (5 g, 50 mmol) and benzhydryl amine (8.41 mL, 50 mmol) in DCM (250 mL) was added molecular sieves (4 Å, powder) followed by NaBH(OAc)$_3$ (32 g, 150 mmol). The reaction mixture was stirred at room temperature overnight before filtered through celite, washed with saturated NaHCO$_3$ (4×), dried over MgSO$_4$, filtered, and concentrated in vacuo to yield a crude product of the amine which was used on next step (13.25 g, 99.9%). 1H NMR (400 MHz, CDCl$_3$) δ 7.42 (bd, J=7.0 Hz, 4H), 7.32 (bt, J=7.2 Hz, 4H), 7.24 (bt, J=7.3 Hz, 2H), 5.07 (s, 1H), 3.96 (dt, J=11.1 Hz, 3.5 Hz, 2H), 3.33 (td, J=11.5 Hz, 2.1 Hz, 2H), 2.66 (m, 1H), 1.93 (m, 2H), 1.54 (bs, 1H), 1.44 (m, 2H).

Step B

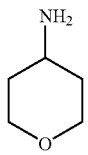

A mixture of the amine (Step A) (13.2 g, 49.4 mmol), 4 N HCl/dioxane (12.5 mL, 49.4 mmol), Pd/C 10% (1.1 g), dioxane (30 mL), and EtOH (120 mL) was placed on a Parr Apparatus and hydrogenated at 35 lb pressure of H$_2$ overnight. The reaction mixture was filtered through celite and concentrated to dryness. The concentrate was stirred in DCM. The precipitate was filtered and dried to yield Intermediate 3 (4.91 g, 72.2%). 1H NMR (400 MHz, CD$_3$OD) δ 3.99 (dd, J=12.1 Hz, 5.1 Hz, 2H), 1.89 (td, J=11.9 Hz, 2.1 Hz, 2H), 3.38-3.32 (m, 1H), 1.96-1.92 (m, 2H), 1.70-1.59 (m, 2H).

INTERMEDIATE 10

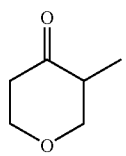

Intermediate 10 was prepared according to the procedure described in *J. Am. Chem. Soc.,* 1991, 113, 2079-2089.

INTERMEDIATE 11

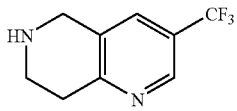

Step A

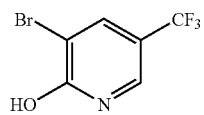

To a solution of 5-trifluoromethyl-2-pyridinal (51 g, 310 mmol) and sodium acetate (26.2 g, 319 mmol) in glacial acetic acid (200 mL) was added bromine (16.7 mL, 325 mmol) and the resulting mixture was heated at 80° C. for 2.5 h. The reaction was allow to cool to room temperature and then was evaporated under reduced pressure. The residue was neutralized with saturated NaHCO$_3$ solution and extracted with ethyl acetate (3×200 mL). The organics were combined, dried over MgSO$_4$, filtered, and evaporated in vacuo to yield 74.45 g (98%) of the crude product. $^1$H NMR (400 MHz, CDCl$_3$) δ 8.04 (d, J=2.6 Hz, 1H), 7.89 (m, 1H).

Step B

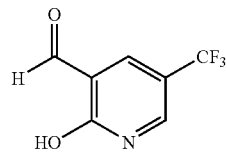

Under nitrogen, the substituted pyridine described in Step A (48.8 g, 202 mmol) was added in small portions to a suspension of NaH (8.9 g, 220 mmol) in anhydrous tetrahydrofuran (500 mL). After complete addition of the intermediate, the reaction mixture was cooled to −78° C. and treated with tert-butyllithium (260 mL, 444 mmol) added dropwise via syringe. After stirring for 5 min, N,N-dimethylformamide (50 mL, 707 mmol) was added slowly to maintain the temperature below −50° C. The resulting mixture was then stirred for 10 h allowing it to warm to room temperature. The mixture was quenched with 2 N HCl and then diluted with ethyl acetate (1000 mL). The organic layer was separated, washed with brine, dried over MgSO4, and evaporated in vacuo. The desired product was precipitated out of ethyl acetate and hexanes and filtered to yield a light brown solid (28.55 g, 74%). $^1$H NMR (500 MHz, CD$_3$OD) δ 10.13 (s, 1H), 8.21 (s, 2H).

Step C

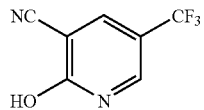

A mixture of the intermediate from Step B (18 g, 95 mmol), sodium formate (7.1 g, 110 mmol), hydroxylamine hydrochloride (7.3 g, 110 mmol), and formic acid (150 mL) was stirred at room temperature for 2 h and then heated to reflux overnight. The reaction mixture was cooled and allowed to stand at room temperature for 7 days. The reaction was poured into water and extracted with ethyl acetate (3×). The combined organic layers were washed with water (2×), saturated NaHCO₃ and brine, dried over Na₂SO₄, filtered, and concentrated in vacuo to yield the desired product as a brown powder (17.84 g, 90%). ¹H NMR (400 MHz, CD₃OD) δ 8.37 (d, J=2.7 Hz, 1H), 8.19 (q, J=0.7 Hz, 0.3 Hz, 1H).

Step D

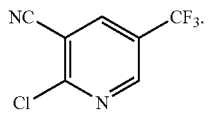

To a mixture of phosphorous oxychloride (13.4 mL, 144 mmol) and quinoline (8.7 mL, 73 mmol) was added the product from Step C (24.6 g, 131 mmol) and the resulting mixture was heated to reflux for 3 h. The reaction was cooled to 100° C. before water (70 mL) was slowly added. The mixture was further cooled to room temperature and neutralized carefully with saturated NaHCO₃ solution. The aqueous layer was extracted with ethyl acetate (3×) and the organic layers were combined, dried over MgSO₄, filtered, and evaporated in vacuo. The crude product was purified by flash chromatography to afford (23.5 g, 87%) of the desired compound. ¹H NMR (500 MHz, CDCl₃) δ 8.88 (d, J=2.0 Hz, 1H), 8.26 (d, J=2.5 Hz, 1H).

Step E

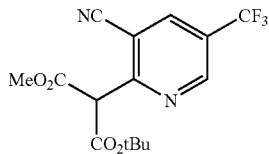

To a suspension of NaH (7.8 g, 200 mmol) in tetrahydrofuran (100 mL) under nitrogen was added dropwise a solution of tert-butyl methyl malonate (20 mL, 120 mmol) in anhydrous tetrahydrofuran (100 mL) via syringe. The reaction mixture was stirred for 0.5 h before a solution of the intermediate prepared in Step D (20.1 g, 97.6 mmol) in tetrahydrofuran (200 mL) was added slowly via syringe. The reaction was stirred at room temperature overnight, then quenched with a saturated solution of NH₄Cl. The organic layer was separated and the aqueous layer was extracted with ethyl acetate (3×). The combined organic layers were washed with water (3×), dried over Na₂SO₄, filtered, and evaporated in vacuo. Flash chromatography afforded 31.76 g (95%) of the pure desired product. ¹H NMR (500 MHz, CDCl₃) δ 9.03 (d, J=1.5 Hz, 1H), 8.25 (d, J=2.0 Hz, 1H), 5.25 (s, 1H), 3.86 (s, 3H), 1.52 (s, 9H).

Step F

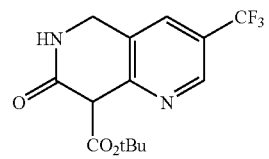

A suspension of Raney Ni (1 g) and the product from Step E (18.2 g, 52.9 mmol) in ethanol (130 mL) was placed on a Parr apparatus and hydrogenated at 40 psi H₂ overnight. The suspension was filtered through celite and the filtrate was evaporated in vacuo to afford 16.35 g (98%) of the crude product. ¹H NMR (500 MHz, CDCl₃) δ 8.83 (s, 1H), 7.89 (s, 1H), 7.82 (s, 1H), 4.83 (d, J=16 Hz, 1H), 4.72 (s, 1H), 4.49 (d, J=16 Hz, 1H), 1.45 (s, 9H).

Step G

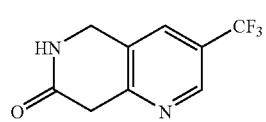

To the mixture of the product from Step F (16 g, 51 mmol) in dichloromethane (60 mL) was added TFA (30 mL) and the resulting mixture was stirred at room temperature for 0.5 h. The solution was evaporated under reduced pressure and the residue was dissolved in dichloromethane. The mixture was neutralized by the slow addition of a solution of saturated sodium bicarbonate and the organic layer was removed. The aqueous layer was extracted with dichloromethane (4×) and the combined organic layers were dried over Na₂SO₄, filtered, and evaporated in vacuo to afford 10.42 g (95%) of the desired product. ¹H NMR (400 MHz, CDCl₃) δ 8.81 (s, 1H), 7.78 (s, 1H), 7.30 (s, 1H), 4.63 (s, 2H), 3.90 (s, 2H).

Step H

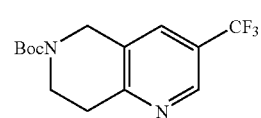

To a solution of the product from Step G (18.0 g, 83.3 mmol) in tetrahydrofuran (50 mL) was added 1.0 M borane in tetrahydrofuran (417 mL, 420 mmol) and the resulting solution was stirred at room temperature overnight. The solution was evaporated under reduced pressure and the residue was treated with 1% HCl/methanol solution. The resutling mixture was heated at 50° C. overnight to breakdown the borane complex. Treatment with acidic methanol was repeated twice to insure that the borane complex was removed. A solution of this crude product (83.3 mmol, assuming 100% conversion) and diisopropylethylamine (43 mL, 250 mmol) in dichloromethane was treated with di-tert-butyl dicarbonate (36.4 g, 167 mmol) and the resulting mixture was stirred at room temperature overnight. The solution was washed with saturated sodium bicarbonate solution, water, and brine. The aqueous layers were combined and back-washed with dichloromethane (2×). The combined organic layers were then dried over Na₂SO₄, filtered, and evaporated to dryness. The crude product was purified by flash chromatography and MPLC to afford (11.89 g, 47%) as a yellow solid. ¹H NMR (500 MHz, CDCl₃) δ 8.69 (s, 1H), 7.66 (s, 1H), 4.67 (s, 2H), 3.79 (t, J=6.0 Hz, 2H), 3.08 (t, J=5.5 Hz, 2H), 1.51 (s, 9H).

Step I

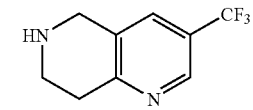

The product described in Step H (11.89 g) was treated with a solution of 4 N HCl in dioxane. The solution was stirred at room temperature for 2 h and then evaporated in vacuo to afford Intermediate 10 (10.85 g, 99%) as a yellow powder. LC-MS for $C_9H_{10}F_3N_2$ calculated 202.07. Found [M+H]⁺ 203.0.

INTERMEDIATE 12

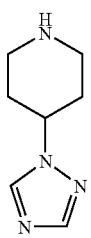

Step A

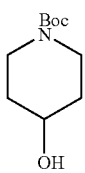

To a stirred solution of 4-hydroxypiperidine (60.8 g) in dichloromethane (500 mL) was added a solution of di-tert-butyl dicarbonate (19 g, 0.55 mol) in dichloromethane (500 mL) very slowly. After the addition, which took 1 h, the resulted mixture was stirred at ambient temperature for 5 h. The mixture was then washed with saturated NaHCO$_3$, 3 N HCl, brine, dried and evaporated to give tert-butyl 4-hydroxypiperidine-1-carboxylate as a thick oil (90 g).

Step B:

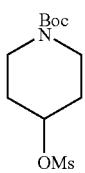

To a stirred solution of tert-butyl 4-hydroxypiperidine-1-carboxylate (21.1 g, 100 mmol) and triethyl amine (22 mL) in dichloromethane (250 mL) at 0° C. was slowly added methanesulfonyl chloride (9.0 mL, 1.1 equiv.). The resulting mixture was stirred for an additional 1 h and during this time white solid was formed. The mixture was then washed with 3 N HCl, dried over Na$_2$SO$_4$ and evaporated to give: tert-butyl 4-[(methylsulfonyl)oxy]piperidine-1-carboxylate as a white solid (29.2 g). $^1$H NMR (400 MHz, CDCl$_3$): δ 4.92-4.87 (m, 1H), 3.75-3.69 (m, 2H), 3.34-3.28 (m, 2H), 3.05 (s, 3H), 2.01-1.94 (m, 2H), 1.87-1.78 (m, 2H).

Step C:

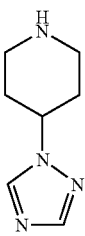

To a stirred solution of: tert-butyl 4-[(methylsulfonyl)oxy]piperidine-1-carboxylate (5.9 g, 21 mmol) and 1,2,4-triazole (1.8 g, 25 mmol equiv.) in DMF at ambient temperature was added sodium hydride (60% in mineral oil, 1.0 g, 25 mmol). The mixture was stirred at 60° C. for 5 days, and the TLC showed no starting mesylate left. The mixture was poured into ice water and extracted with ethyl acetate (3×). The organic layer was dried, evaporated and purified by silica flash column eluting with 0-10% methanol in ethyl acetate to give tert-butyl 4-(1H-1,2,4-triazol-1-yl)piperidine-1-carboxylate as a white solid. The solid was then treated with hydrogen chloride in dioxane (4 N, 10 mL) for 2 h. The mixture was then evaporated to remove most of the dioxane to give a white solid, which was washed with ethyl acetate to give the desired 4-(1H-1,2,4-triazol-1-yl)piperidine hydrochloride salt (5.55 g). $^1$H NMR (300 MHz, CD$_3$OD): δ 10.00 (s, 1H), 8.97 (s, 1H), 5.10-5.00 (m, 1H), 3.63-3.58 (br. d, 2H), 3.33-3.26 (br. d, 2H), 2.50-2.30 (m, 4H).

The following intermediates 13-17 were prepared in a similar fashion to Intermediate 12 using: tert-butyl 4-[(methylsulfonyl)oxy]piperidine-1-carboxylate and the appropriate heterocycles.

INTERMEDIATE 13

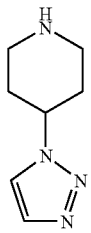

Prepared from 1,2,3-triazole according to the procedure for Intermediate 12. 4-(1H-1,2,3-triazol-1-yl)piperidine hydrochloride: $^1$H NMR (400 MHz, CD$_3$OD): δ 8.77 (s, 1H), 8.54 (s, 1H), 5.26-5.19 (m, 1H), 3.65-3.59 (m, 2H), 3.37-3.29 (m, 2H), 2.60-2.54 (m, 2H), 2.50-2.39 (m, 2H).

INTERMEDIATE 14

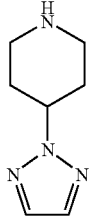

Prepared from 1,2,3-triazole according to the procedure for Intermediate 12. 4-(2H-1,2,3-triazol-2-yl)piperidine hydrochloride: $^1$H NMR (400 MHz, CD$_3$OD): δ 7.72 (s, 2H), 4.94-4.87 (m, 1H), 3.54-3.48 (m, 2H), 3.28-3.22 (m, 2H), 2.46-2.32 (m, 4H).

INTERMEDIATE 15

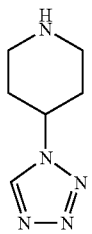

Prepared from tetrazole according to the procedure for Intermediate 12. 4-(H-tetraazol-1-yl)piperidine hydrochloride: $^1$H NMR (400 MHz, CD$_3$OD): δ 8.77 (s, 1H), 5.30-5.23 (m, 1H), 3.58-3.53 (m, 2H), 3.35-3.29 (m, 2H), 2.58-2.2.52 (m, 2H), 2.48-2.38 (m, 2H).

INTERMEDIATE 16

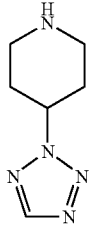

Prepared from tetrazole according to the procedure for Intermediate 12. 4-(2H-tetraazol-2-yl)piperidine hydrochloride: $^1$H NMR (400 MHz, CD$_3$OD): δ 9.32 (s, 1H), 5.08-5.00 (m, 1H), 3.61-3.57 (m, 2H), 3.33-3.28 (m, 2H), 2.52-2.47 (m, 2H), 2.42-2.32 (m, 2H).

INTERMEDIATE 17

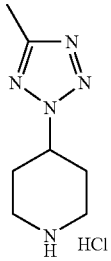

Prepared from 5-methyltetrazole according to the procedure for Intermediate 12. $^1$H NMR (400 MHz, CD$_3$OD): δ 5.08-5.00 (m, 1H), 3.61-3.57 (m, 2H), 3.33-3.28 (m, 2H), 2.52-2.47 (m, 2H), 2.42-2.32 (m, 2H), 1.68 (s, 3H).

EXAMPLE 1

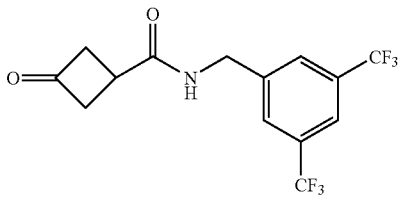

Step A

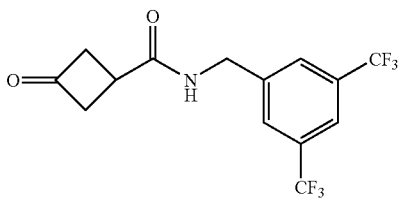

Intermediate 1 (200 mg, 1.75 mmol), bis-trifluoromethyl-benzylamine (490 mg, 1.75 mmol), DIEA (306 μL, 1.75 mmol), HOAT (240 mg, 1.75 mmol), EDC (504 mg, 2.63 mmol) and DCM (15 ml) were mixed and stirred at room temperature for 18 hours. The reaction mixture was diluted with DCM, washed with 1N HCl, saturated NaHCO$_3$ solution, water and brine, dried over anhydrous MgSO$_4$, and concentrated in vacuo to yield the product (529 mg, 89%). NMR (300 MHz, CDCl$_3$) δ 7.81 (s, 1H), 7.74 (s, 2H), 6.13 (s, 1H), 4.62 (d, J=6.04 Hz, 2H), 3.56-3.47 (m, 2H), 3.29-3.20 (m, 2H), 3.07 (m, 1H).

Step B

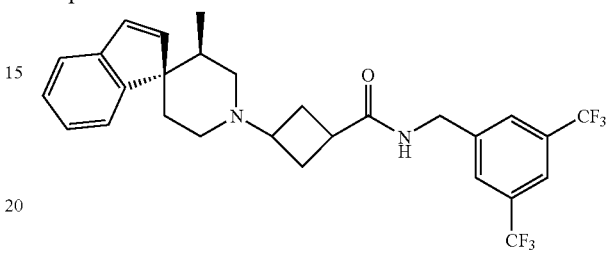

Product from Step A (100 mg, 0.295 mmol), Intermediate 2 (70 mg, 0.295 mmol), DIEA (103 μL, 0.590 mmol), molecular sieves, NaBH(OAc)$_3$ (313, 1.474 mmol), and DCE (10 ml) were mixed and stirred at room temperature for 18 hours. The reaction was purified by preparative TLC (3:0.3: 96.7, MeOH:NH$_4$OH:DCM). Cis and trans isomers were also separated (cis 90 mg, trans 23 mg, 73.4%) Cis was the less polar and more active isomer. Cis isomer: NMR (500 MHz, CDCl$_3$) δ 7.81 (s, 1H), 7.78 (s, 2H), 7.30 (d, J=7.1 Hz, 1H), 7.24 (dt, J=7.2 Hz, 1.6 Hz, 1H), 7.18 (m, 2H), 6.96 (s, 1H), 6.81 (d, J=5.8 Hz, 1H), 6.64 (d, J=6.0 Hz, 1H), 4.61 (d, J=5.9 Hz, 2H), 3.01 (s, 1H), 2.95-2.84 (m, 3H), 2.50 (t, J=5.6 Hz, 2H), 2.25-2.13 (m, 5H), 1.90 (m, 1H), 1.33 (m, 1H), 0.32 (d, J=6.9 Hz, 3H). LC-MS for C$_{28}$H$_{28}$F$_6$N$_2$O MW calculated 522.21. Found 523.2.

A variety of amine substitution on the R position of cyclobutane ring was prepared using the same reaction procedure illustrated in Example 1. The table below summarizes these compounds.

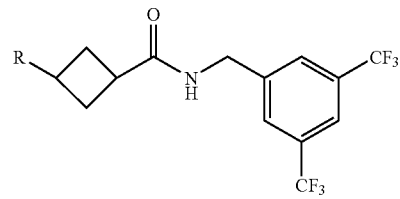

| Example | R | Molecular Formular | Calculated MW | Found M$^+$H$^+$ |
|---|---|---|---|---|
| 2 | phenyl-piperidinyl | C$_{25}$H$_{26}$F$_6$N$_2$O | 484.19 | 485.2 |
| 3 | 4-fluorophenyl-piperidinyl | C$_{25}$H$_{25}$F$_7$N$_2$O | 502.19 | 503.0 |
| 4 | phenyl-tetrahydropyridinyl | C$_{25}$H$_{24}$F$_6$N$_2$O | 482.18 | 483.0 |

-continued

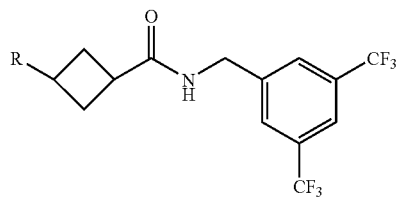

| Example | R | Molecualr Formular | Calculated MW | Found M+H+ |
|---|---|---|---|---|
| 5 | 2-(piperazin-1-yl)phenyl | C₂₅H₂₇F₆N₃O | 499.21 | 500.0 |
| 6 | spiro[indene-1,4'-piperidine] | C₂₇H₂₆F₆N₂O | 508.19 | 509.0 |
| 7 | N-Ms spiro[indoline-3,4'-piperidine] | C₂₇H₂₉F₆N₃O₃S₂ | 589.18 | 590.0 |
| 8 | 4-benzylpiperidine | C₂₆H₂₈F₆N₂O | 499.21 | 500.0 |
| 9 | 4-hydroxy-4-phenylpiperidine | C₂₅H₂₆F₆N₂O₂ | 500.19 | 501.0 |
| 10 | 4-cyano-4-phenylpiperidine | C₂₆H₂₅F₆N₃O | 509.19 | 510.0 |

EXAMPLE 11

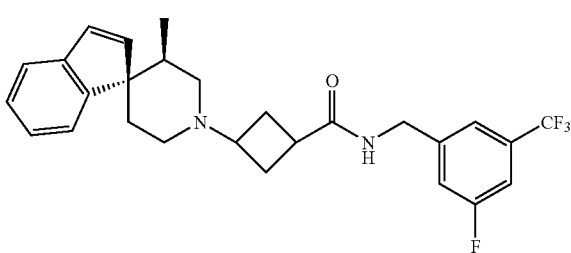

Step A

Intermediate 3 (100 mg, 0.49 mmol), Intermediate 2 (116 mg, 0.49 mmol), DIEA (171 µL, 0.98 mmol), molecular sieves, NaBH(OAc)₃ (520 mg, 2.45 mmol), and DCM (10 ml) were mixed together and stirred at room temperature for 60 hours. The reaction was purified by preparative TLC (2:0.2:97.8, MeOH:NH₄OH:DCM) to yield the product (95 mg, 50%). LC-MS for C₂₆H₂₉NO₂ MW calculated 387.22. Found 388.15.

Step B

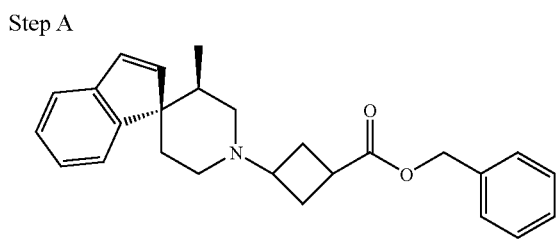

The product from Step A (90 mg, 0.232 mmol), 5N NaOH solution (325 µL, 1.63 mmol), EtOH (3 ml) and water (2.65 mL) were mixed together and stirred at room temperature. Upon disappearance of starting material, reaction mixture was concentrated in vacuo and redissolved in water. The aqueous layer was neutralized to pH 7.0 with 2N HCl solution before extracted with DCM (7×). The organic layer contained mostly benzyl alcohol. The aqueous layer was concentrated down and redissolved in DCM. The organic layer was filtered and concentrated in vacuo to yield the product (60 mg, 87.0%).

Step C

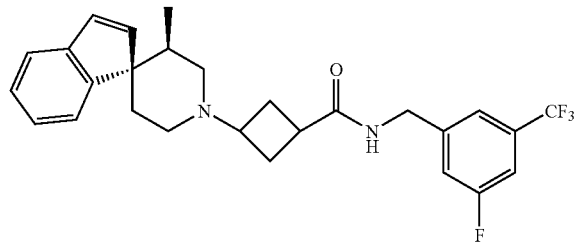

The product from Step B (60 mg, 0.202 mmol), 3-fluoro-5-trifluoromethylbenzylamine (30 μL, 0.202 mmol), HOAT (28 mg, 0.202 mmol), and EDC (60 mg, 0.303 mmol) were mixed together and stirred at room temperature for 18 hours. The reaction mixture was purified by preparative TLC (3:0.3:96.7, MeOH:NH$_4$OH:DCM). Cis and trans isomers were separated (cis 12 mg, trans 1 mg, 13.7%). LC-MS for $C_{27}H_{28}F_4N_2O$ MW calculated 472.21. Found 473.2.

EXAMPLE 12

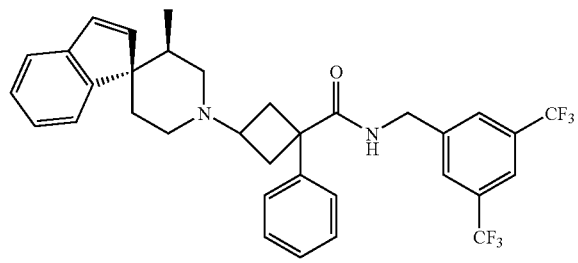

Step A

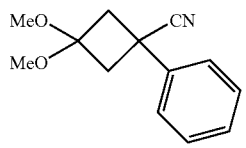

A solution of 60% NaH (10 g, 250 mmol) suspended in DMF (100 ml) was cooled to 0° C. before benzylcyanide (11.7 g, 100 mmol) was added slowly. The solution was stirred at 0° C. for another 10 minutes before dimethoxy-dibromomethane (13.1 g, 50 mmol) was added. The reaction mixture was stirred at 60° C. for 18 hours before cooled to room temperature, poured into water, and extracted with ether. The combined organic layer was concentrated in vacuo. The crude product was purified by flash chromatography (20:80, ethylacetate:hexanes) to yield the desired product (6.4 g, 59%). NMR (300 MHz, CDCl3) δ 7.50-7.32 (m, 5H), 3.23 (d, J=30.6 Hz, 6H), 3.11 (dm, J=13.6 Hz, 2H), 2.73 (dm, J=11.7 Hz, 2H).

Step B

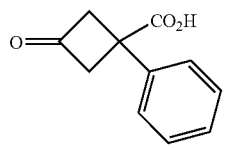

A solution of The product from Step A (4.4 g, 20 mmol), 5 M NaOH (20 mL), EtOH (50 mL), and water (50 mL) were heated at reflux overnight before concentrated to dryness. The concentrated was redissolved in water (20 mL), dioxane (30 mL), and 12 M HCl (10 mL). The reaction mixture was stirred at room temperature for 3 hours before concentrated in vacuo. The reaction was redissolved in 1N HCl and extracted with EtOAc (2×). Combined organic layer was dried over anhydrous MgSO$_4$ and concentrated in vacuo to yield a white solid of 12-B. The crude product was used on next step. NMR (500 MHz, CDCl$_3$) δ 7.43-7.36 (m, 5H), 3.95 (dm, J=20.1 Hz, 2H), 3.62 (dm, J=20.4 Hz, 2H).

Step C

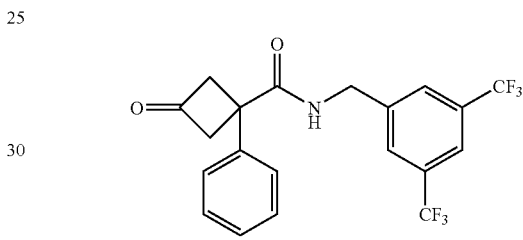

A solution of the product from Step B (500 mg, 2.63 mmol), 3,5-bistrifluoromethylbenzylamine (735 mg, 2.63 mmol), DIEA (686 μL, 3.94 mmol), HOAT (358 mg, 2.63 mmol), EDC (755 mg, 3.94 mmol), and DCM (20 mL) were stirred at room temperature overnight. The reaction mixture was washed with 1 M HCl (2×), saturated NaHCO$_3$ and water (3×), dried over anhydrous MgSO$_4$, and concentrated in vacuo to yield the desired product as a white powder (630 mg, 57.8%). The crude product was used in next step. NMR (500 MHz, CDCl3) δ 7.76 (s, 1H), 7.53 (s, 2H), 7.50 (m, 2H), 7.42 (m, 3H), 5.75 (s, 1H), 4.51 (d, J=6.2 Hz, 2H), 4.00-3.96 (dm, J=19.2 Hz, 2H), 3.56-3.52 (dm, J=19.2 Hz, 2H).

Step D

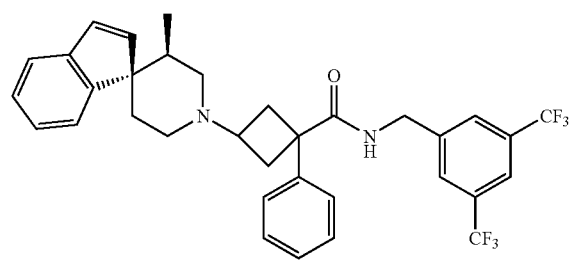

A solution of the product from Step C (200 mg, 0.482 mmol), Intermediate 2 (115 mg, 0.482 mmol), DIEA (126 μL, 0.723 mmol), 4 Å powdered molecular sieves, NaBH(OAc)$_3$ (515 mg, 2.41 mmol), and DCM (20 ml) was stirred at room temperature overnight before being filtered through celite and purified by preparative TLC (3:0.3:96.7, MeOH:NH$_4$OH:

DCM). The cis and trans isomers were also separated (less polar isomer 82.4 mg, more polar isomer 128 mg, 74.9%). More polar isomer: 1H NMR (500 MHz, CDCl3) δ 7.75 (s, 1H), 7.55 (s, 2H), 7.46 (m, 2H), 7.38-7.32 (m, 1H), 7.32-7.27 (m, 1H), 7.27-7.2 (m, 2H), 6.80 (d, J=5.7 Hz, 1H), 6.61 (d, J=5.7 Hz, 1H), 4.51 (d, J=6.2 Hz, 2H), 3.08-2.77 (m, 7H), 2.31-2.18 (m, 3H), 1.93 (t, J=10.9 Hz, 1H), 1.34 (d, J=12.8 Hz, 1H), 0.33 (d, J=7.1 Hz, 3H). LC-MS for $C_{34}H_{32}F_6N_2O$ MW calculated 598.24. Found 599.25.

A variation of compounds with phenyl substitution at R1 position, amine substitution at R2 position, and fluorine substitution at R3 position were prepared using the reaction scheme detailed in Example 12. Phenyl derivatives were synthesized from different substituted phenylnitriles using the procedure detailed in Step A. 3-fluoro-5-trifluoromethylbenzylamine was substituted in Step C. Amine SAR was followed the same procedure detailed in Step D. All of the components are either commercially available or are described in the Intermediates section. These compounds are summarized in the table below.

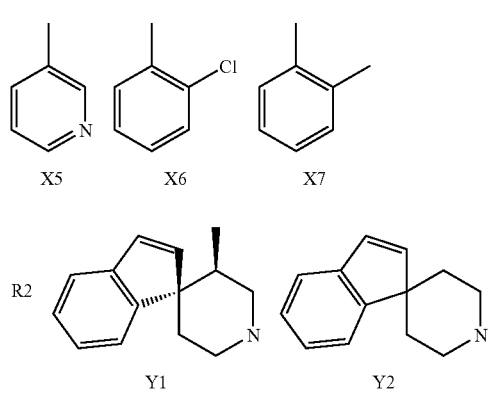

| Example | R1 | R2 | R3 | Molecular Formula | Calculated MW | Found [M+H+] |
|---------|----|----|----|-------------------|---------------|--------------|
| 13 | X1 | Y2 | CF3 | C33H30F6N2O | 584.23 | 585.25 |
| 14 | X1 | Y3 | CF3 | C31H30F6N2O | 560.26 | 561.25 |
| 15 | X1 | Y4 | CF3 | C25H26F6N2O | 484.48 | 485.20 |
| 16 | X1 | Y5 | CF3 | C25H26F6N2O2 | 500.19 | 501.25 |
| 17 | X1 | Y1 | F | C33H32F4N2O | 548.25 | 549.25 |
| 18 | X1 | Y2 | F | C32H30F4N2O | 534.23 | 535.30 |
| 19 | X1 | Y3 | F | C30H30F4N2O | 510.23 | 511.30 |
| 20 | X1 | Y4 | F | C24H26F4N2O | 434.20 | 435.25 |
| 21 | X1 | Y5 | F | C24H26F4N2O2 | 450.19 | 451.30 |
| 22 | X2 | Y1 | F | C34H34F4N2O2 | 578.26 | 579.25 |
| 23 | X2 | Y3 | F | C31H32F4N2O2 | 540.24 | 541.30 |
| 24 | X2 | Y4 | F | C25H28F4N2O2 | 464.21 | 465.25 |
| 25 | X3 | Y1 | F | C33H31F5N2O | 566.24 | 567.25 |
| 26 | X3 | Y3 | F | C30H29F5N2O | 528.22 | 529.25 |
| 27 | X3 | Y4 | F | C24H25F5N2O | 452.19 | 453.25 |
| 28 | X4 | Y1 | F | C33H31BrF4N2O | 626.18 | 629.20 |
| 29 | X4 | Y3 | F | C30H29BrF4N2O | 588.16 | 591.15 |
| 30 | X4 | Y4 | F | C24H25BrF4N2O | 512.13 | 515.05 |
| 31 | X5 | Y1 | F | C32H31F4N3O | 549.24 | 550.30 |
| 32 | X5 | Y3 | F | C29H29F4N3O | 511.22 | 512.20 |
| 33 | X5 | Y4 | F | C23H25F4N3O | 435.19 | 436.15 |
| 34 | X5 | Y1 | CF3 | C33H31F6N3O | 599.24 | 600.25 |
| 35 | X6 | Y1 | F | C33H31ClF4N2O | 582.21 | 583.3 |
| 36 | X6 | Y3 | F | C30H29ClF4N2O | 544.19 | 545.20 |
| 37 | X6 | Y4 | F | C24H25ClF4N2O | 468.16 | 469.15 |
| 38 | X7 | Y1 | F | C34H34F4N2O | 562.26 | 563.25 |
| 39 | X7 | Y3 | F | C31H32F4N2O | 524.25 | 525.25 |
| 40 | X7 | Y4 | F | C25H28F4N2O | 448.21 | 449.15 |

EXAMPLE 41

A solution of Example 16 (40 mg, 0.08 mmol), 37% formaldehyde (20 μL, 0.24 mmol), DIEA (25 μL, 0.12 mmol), TFA (5 μL), NaCNBH (25 mg, 0.40 mmol), and MeOH (1.5 mL) was stirred at room temperature and the reaction was monitored by TLC. The crude reaction was purified by preparative TLC (5:0.5:94.5, MeOH:NH4OH:DCM). Cis and trans isomers were separated with the more polar isomer being the cis and more active isomer. LC-MS for $C_{26}H_{28}F_6N_2O_2$ MW calculated 514.21. Found 515.35.

EXAMPLE 42

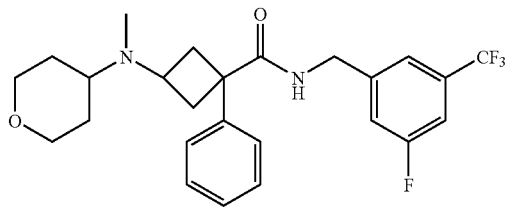

Example 42 was synthesized from Example 21 using the procedure detailed in Example 41. Cis and trans isomers were synthesized separately from the cis and trans isomers of Example 41, with the trans being the more polar and active isomer. LC-MS for $C_{25}H_{28}F_4N_2O_2$ MW calculated 464.21. Found 465.25.

EXAMPLE 43

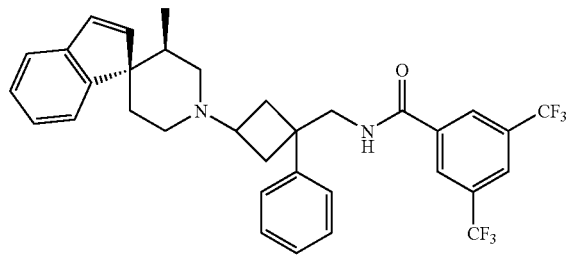

Step A

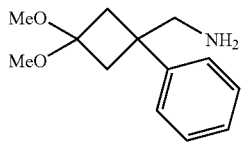

A solution of the product from Step A, Example 12 (2.0 g, 9.2 mmol), Raney Ni (200 mg), NH$_4$OH (10 mL) and EtOH (50 ml) was shaken on a Parr-Apparatus at 40 psi for 24 hours. Upon disappearance of starting material on HPLC, the reaction mixture was filtered through celite and concentrated in vacuo. The crude product was used on next step.

Step B

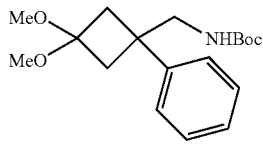

The product from Step A (2.0 g, 9.2 mmol) was dissolved in DCM before di-tert-butyl dicarbonate (2.4 g, 11 mmol) was added. The reaction mixture was stirred at room temperature for 18 hours before concentrated in vacuo to yield the product, which was used directly in the next step.

Step C

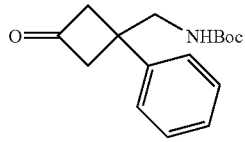

The product from Step C (2.96 g, 9.2 mmol) was dissolved in dioxane (20 ml) and water (20 mL) before 1 M HCl (2 mL) was added. The reaction mixture was stirred at room temperature for 18 hours before being extracted with EtOAc. The organic layer was washed with saturated NaHCO$_3$ solution and concentrated in vacuo to yield the product. The crude product was used on next step.

Step D

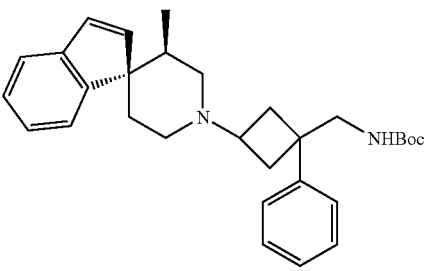

A solution of the product from Step C (500 mg, 1.82 mmol), Intermediate 2 (430 mg, 1.82 mmol), DIEA (475 μL, 2.73 mmol), 4 Å molecular sieves, NaBH(OAc)$_3$ (1.90 g, 9.10 mmol), and DCM (40 mL) was stirred at room temperature overnight before being filtered through celite and purified by preparative TLC (3:0.3:96.7, MeOH:NH$_4$OH:DCM) to yield the desired product (696 mg, 83.6%). LC-MS for $C_{30}H_{38}N_2O_2$ MW calculated 458.29. Found 459.

Step E

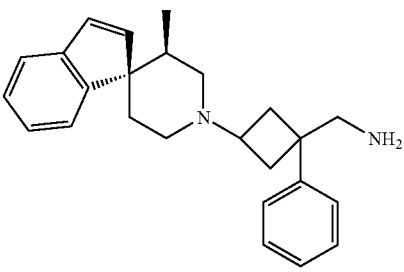

the product from Step D (400 mg, 0.873 mmol) was stirred in a solution of 95% TFA in water (5 mL). The reaction was monitored by HPLC. Upon completion of reaction, the mixture was concentrated in vacuo, redissolved in a minimum amount of DCM, and washed with saturated NaHCO$_3$ (4×) to get rid of TFA. The organic layer was dried over anhydrous MgSO$_4$ and concentrated in vacuo to yield the desired product (208 mg, 66.5%). The crude product was used on next step.

Step F

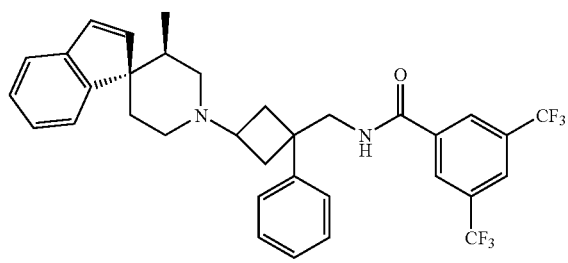

A solution of the product from Step E (10 mg, 0.028 mmol), 3,5-bistrifluoromethylbenzoic acid (7.2 mg, 0.028 mmol), HOAT (3.8 mg, 0.028 mmol), EDC (8.0 mg, 0.028 mmol), and DCM (0.75 mL) was stirred at room temperature overnight. The crude reaction mixture was purified by preparative TLC (3:0.3:96.7, MeOH:NH$_4$OH:DCM) to yield Example 43. Cis and trans isomers were separated with cis being the more polar and active isomer. LC-MS for C$_{33}$H$_{32}$F$_6$N$_2$O$_1$ MW calculated 598.24. Found 599.35.

A variety of compounds with different benzoic amide was prepared using the reaction scheme detailed in Example 43 using different benzoic acids, that were commercially available. These compounds are summarized in the table below.

| Example | R | Molecualr Formular | Calculated MW | Found M+H+ |
|---|---|---|---|---|
| 44 | Me | C27H32N2O | 400.25 | 401.2 |
| 45 | 2-MeO-C6H4 | C33H36N2O2 | 492.28 | 493.3 |
| 46 | 3,4-diF-C6H3 | C32H32F2N2O2 | 498.25 | 499.3 |
| 47 | 4-CF3-C6H4 | C33H33F3N2O | 530.25 | 531.25 |
| 48 | 2-CF3-C6H4 | C33H33F3N2O | 530.25 | 531 |
| 49 | C6H5 | C32H34N2O | 462.27 | 463.3 |
| 50 | 3-CF3-C6H4 | C33H33F3N2O | 530.25 | 531.25 |
| 51 | 3-CF3-5-F-C6H3 | C33H32F4N2O | 548.25 | 549.25 |

-continued

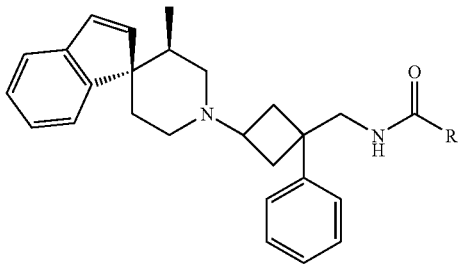

| Example | R | Molecualr Formular | Calculated MW | Found M+H+ |
|---|---|---|---|---|
| 52 | [benzyl] | C33H36N2O | 476.28 | 477.25 |
| 53 | [3-(trifluoromethyl)benzyl] | C34H35F3N2O | 544.27 | 545.35 |

EXAMPLE 54

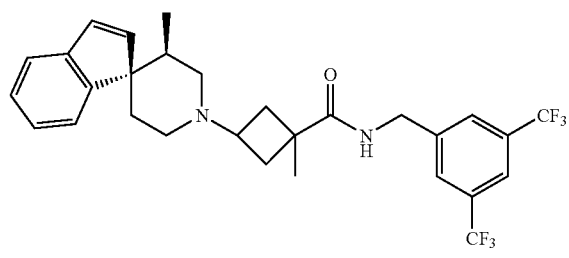

Step A

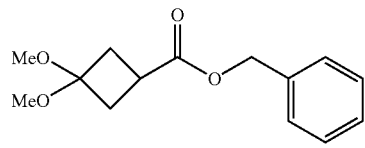

Intermediate 3 (4.93 g, 24.2 mmol) was dissolved in DCM (50 mL) and MeOH (50 mL) first before TMOF (26.5 mL, 242 mmol) was added. TsOH (460 mg, 2.42 mmol) was added last. The reaction mixture was stirred for 2.5 hours before being concentrated in vacuo. The concentrate was diluted with EtOAc, quenched with saturated NaHCO$_3$ solution, washed with brine, dried over anhydrous MgSO$_4$, and concentrated in vacuo. The crude product was purified by MPLC (20:80, EtOAc:hexanes) to yield the desired product (5.71 g, 94.5%). 1H NMR (500 MHz, CDCl$_3$) δ 7.37 (m, 5H), 5.16 (s, 2H), 3.17 (d, J=11.6 Hz, 6H), 2.95 (m, 1H), 2.44 (m, 4H).

Step B

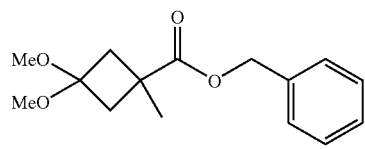

To a flamed dried round-bottomed flask were added the product from Step A (300 mg, 1.20 mmol), MeI (150 μL, 2.40 mmol), and THF (7 mL) at −78° C. under N$_2$. 0.5 M KHMDS in THF (4.8 mL, 2.40 mmol) was added last. The reaction mixture was stirred at −78° C. for 6 hours before being warmed to room temperature and stirred overnight. The reaction mixture was poured into saturated NH$_4$Cl solution and extracted with ether (4×). Combined organic layer was dried over anhydrous MgSO$_4$ and concentrated in vacuo. The crude product was purified by preparative TLC (20:80, EtOAc: hexanes) to yield the desired product (228 mg, 71.9%). 1H NMR (400 MHz, CDCl3) δ 7.37 (m, 5H), 5.16 (s, 2H), 3.15 (d, J=18.4 Hz, 6H), 2.68 (dm, J=13.3 Hz, 2H), 2.08 (dm, J=13.1 Hz, 2H), 1.47 (s, 3H).

Step C

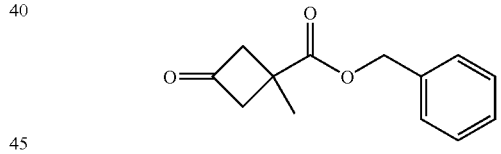

The product from Step B (220 mg, 0.83 mmol) was stirred in a solution of 90% TFA in water (10 mL). Upon completion of reaction, the mixture was concentrated to dryness and redissolved in ether. The organic layer was washed with saturated NaHCO$_3$ (4×) and water, dried over anhydrous MgSO$_4$, and concentrated in vacuo to yield the desired product (150 mg, 82.4%). 1H NMR (500 MHz, CDCl$_3$) δ 7.37 (m, 5H), 5.22 (s, 2H), 3.61 (dm, J=19.9 Hz, 2H), 2.93 (dm, J=19.9 Hz, 2H), 1.62 (s, 3H).

Step D

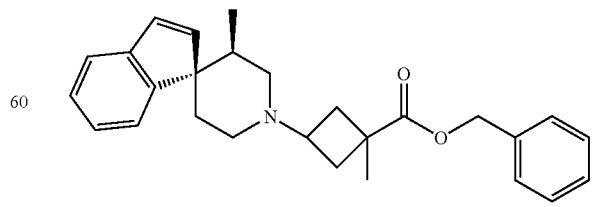

A solution of the product from Step C (150 mg, 0.688 mmol), Intermediate 2 (165 mg, 0.688 mmol), DIEA (180 μL, 1.03 mmol), molecular sieves, NaBH(OAc)$_3$ (730 mg, 3.44 mmol) in DCM (15 mL) was stirred at room temperature overnight. The reaction mixture was filter through celite, concentrated in vacuo, and purified by preparative TLC (3:0.3:96.7, MeOH:NH$_4$OH:DCM) to yield the desired product as a mixture of cis and trans isomers (267 mg, 96.7%). LC-MS for C$_{27}$H$_{31}$NO$_2$ MW calculated 401.24. Found 402.2.

Step E

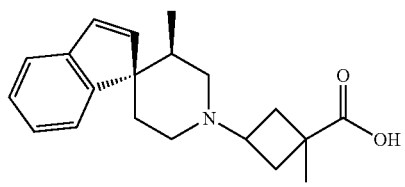

The product from Step D (260 mg, 0.648 mmol), 5 M NaOH solution (650 μL, 324 mmol), EtOH (5 mL) and water (1 mL) were mixed together and stirred at room temperature. Upon disappearance of starting material, the reaction mixture was concentrated in vacuo and redissolved in water. The aqueous layer was first washed with ether to get rid of the benzyl alcohol before being neutralized to pH 7.0 with 2 M HCl solution. The aqueous layer was extracted with DCM (5×). The combined organic layer was dried over anhydrous MgSO$_4$, filtered, and concentrated in vacuo to yield the desired product (112 mg, 55.6%).

Step F

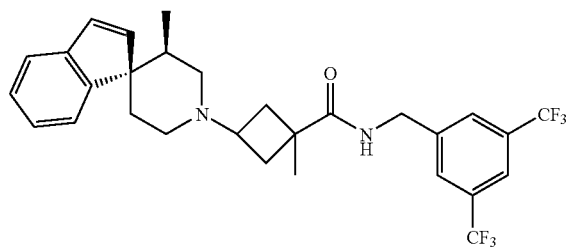

The product from Step E (30 mg, 0.096 mmol), bis-trifluoromethylbenzylamine hydrochloride (30 mg, 0.096 mmol), DIEA (25 μL, 0.15 mmol), HOAT (15 mg, 0.096 mmol), and EDC (28 g, 0.15 mmol) were mixed together in DCM and stirred at room temperature overnight. The reaction mixture was purified by preparative TLC (3:0.3:96.7, MeOH: NH$_4$OH:DCM). Cis and trans isomers were separated with cis being the less polar and more active isomer (cis 43 mg, trans 3.5 mg, 89.0%). LC-MS for C$_{29}$H$_{30}$F$_6$N$_2$O MW calculated 536.23. Found 537.25.

A variety of compounds with different alkyl substitution at the R1 and R2 position were prepared using the reaction procedures detailed in Example 57. Alkylating used were EtI, PrI, and methyl disulfide (MeS). The stereoisomers of the propyl and thiomethyl compounds were separated on a chiral OD column. The table below summarizes these compounds.

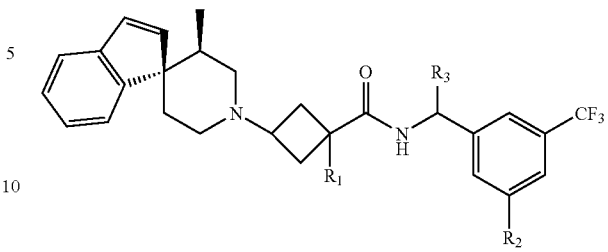

| Example | R1 | R2 | R3 | Molecular Formula | Calculated MW | Found [M+H+] |
|---|---|---|---|---|---|---|
| 55 | Me | F | H | C28H30F4N2O | 486.23 | 487.3 |
| 56 | Et | CF3 | H | C30H32F6N2O | 550.24 | 551.2 |
| 57 | Et | F | H | C29H32F4N2O | 500.24 | 501.25 |
| 58 | Pr | CF3 | H | C31H34F6N2O | 564.26 | 565.3 |
| 59 | Pr | F | H | C30H34F6N2O | 514.26 | 515.3 |
| 60 | MeS | CF3 | H | C29H30F6N2OS | 568.20 | 569.2 |
| 61 | MeS | F | H | C28H30F4N2OS | 518.20 | 519.25 |
| 62 | Pr | H | Me | C31H37F3N2O | 510.29 | 511.3 |
| 63 | Me | CF3 | Me | C32H36F6N2O | 578.27 | 579.25 |

EXAMPLE 64

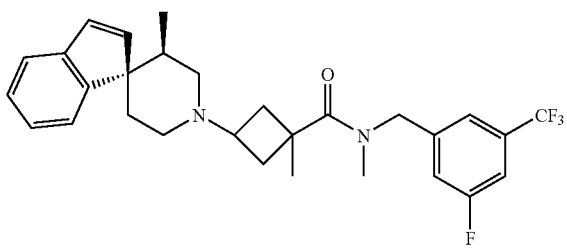

The product from Example 54, Step E (25 mg, 0.080 mmol), Intermediate 6 (20 mg, 0.080 mmol), DIEA (21 μL, 0.12 mmol), HOAT (12 mg, 0.080 mmol), and EDC (25 mg, 0.12 mmol) were mixed together in DCM (2 mL) and stirred at room temperature overnight. The reaction mixture was purified by preparative TLC (50:50, EtOAc:hexanes) to yield Example 64 (12.5 mg, 31.3%). LC-MS for C$_{29}$H$_{32}$F$_4$N$_2$O MW calculated 500.25. Found 501.25.

EXAMPLE 65

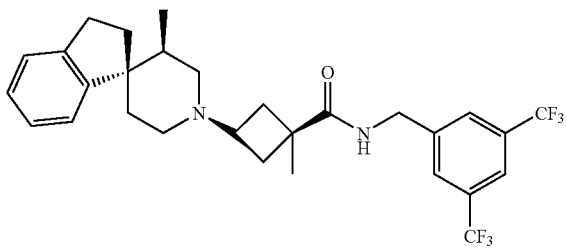

Example 57 (15 mg, 0.028 mmol) and Pd/C (5 mg) were stirred in EtOH (7 mL) under hydrogen overnight. The reaction was filtered through celite and concentrated in vacuo to yield Example 65 (13.6 mg, 90.7%). LC-MS for C$_{29}$H$_{32}$F$_6$N$_2$O MW calculated 538.24. Found 5.39.2.

EXAMPLE 66

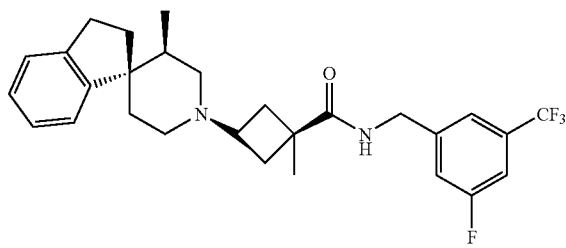

Example 58 (15 mg, 0.028 mmol) and Pd/C (5 mg) were stirred in EtOH (7 mL) under hydrogen overnight. The reaction was filtered through celite and concentrated in vacuo to yield Example 66 (15 mg, 100%). LC-MS for C$_{28}$H$_{32}$F$_4$N$_2$O MW calculated 488.25. Found 489.25.

EXAMPLE 67

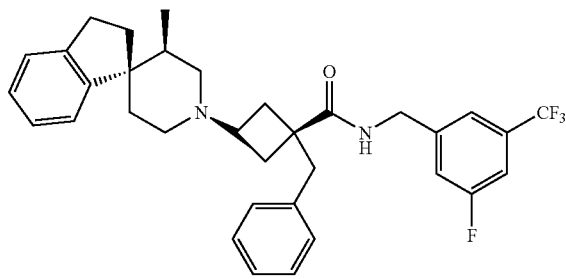

Step A

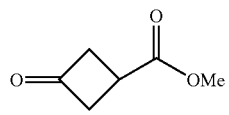

A solution of Intermediate 1 (2.0 g, 18 mmol), MeOH (710 µL, 17.5 mmol), DMAP (215 mg, 1.75 mmol), EDC (5.04 g, 26.3 mmol) and DCM (100 mL) were mixed and stirred at room temperature overnight. The reaction mixture was washed with water (3×). Combined aqueous layer was extracted with DCM. Combined organic layer was washed with brine, dried over anhydrous MgSO$_4$, and concentrated in vacuo to yield the desired product. 1H NMR (400 MHz, CDCl$_3$) δ 3.79 (s, 3H), 3.48-3.25 (m, 5H).

Step B

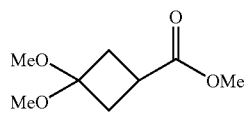

The product from Step A (2.25 g, 17.6 mmol) was dissolved in MeOH (25 mL) and DCM (25 mL) first before trimethyl orthoformate (19 mL, 180 mmol) was added. TsOH (335 mg, 1.76 mmol) was added last. The mixture was stirred at room temperature for 2 hours before concentrated in vacuo. The concentrate was redissolved in EtOAc, quenched with saturated NaHCO$_3$, washed with brine, dried over anhydrous MgSO$_4$, and concentrated in vacuo. The crude product was purified by MPLC (20:80, EtOAc:hexanes) to yield the desired product (1.72 g, 56.2% for last two steps). 1H NMR (400 MHz, CDCl$_3$) δ 3.71 (s, 3H), 3.17 (d, J=8.2 Hz, 6H), 2.90 (p, J=8.7 Hz, 1H), 2.49-2.36 (m, 4H).

Step C

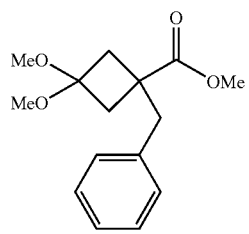

To a flame-dried flask was dissolved KHMDS (690 mg, 3.44 mmol) in THF (10 mL) under nitrogen. The mixture was cooled to −78° C. before The product from Step B (300 mg, 1.72 mmol) and BnBr (615 µL, 5.17 mmol) were added. The mixture was stirred at −78° C. for 15 minutes before raised to room temperature. The reaction was monitored by TLC. Upon completion of reaction, the mixture was dumped in saturated NH$_4$Cl solution and extracted with ether (3×). Combined organic layer was dried over anhydrous MgSO$_4$ and concentrated in vacuo. The crude product was purified by preparative TLC (20:80, EtOAc:hexanes) to yield the desired product (261 mg, 57.4%). 1H NMR (500 Mz, CDCl$_3$) δ 7.33-7.2 (m, 3H), 7.10 (d, 2H), 3.67 (s, 3H), 3.17 (d, J=25.4 Hz, 6H), 2.60 (app d, J=13.3 Hz, 2H), 3.14 (s, 2H), 2.26 (app d, J=13.5 Hz, 2H).

Step D

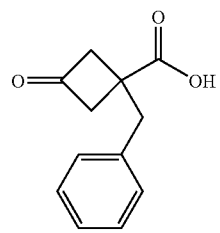

A solution of The product form Step C (261 mg, 0.988 mmol), 5 M NaOH (1 mL, 5 mmol) and EtOH (7 mL) was heated to reflux for 30 minutes before being concentrated to dryness. The concentrate was redissolved in 2 M HCl and dioxane. The solution was stirred at room temperature and the reaction was monitored by HPLC. Upon completion of the reaction, the mixture was concentrated in vacuo to yield the crude product (157 mg, 77.7%). The crude product was used in next step without purification. 1H NMR (500 MHz, CDCl$_3$) δ 7.35-7.28 (m, 3H), 7.23 (app d, J=7.1, 2H), 3.54 (app d, J=19.9 Hz, 2H), 3.30 (s, 2H), 3.16 (app d, J=20.1 Hz, 2H).

Step E

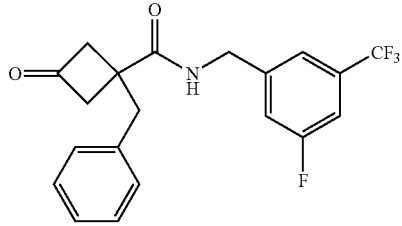

A solution of the product form Step D (150 mg, 0.735 mmol), 3-fluoro-5-trifluoromethylbenzylamine (110 µL, 0.735 mmol), HOAT (100 mg, 0.735 mmol), EDC (215 mg, 1.10 mmol) and DCM (10 mL) were mixed together and stirred at room temperature overnight. The crude reaction was purified by preparative TLC (30:70, EtOAc:hexanes) to yield the desired product (177 mg, 63.7%). 1H NMR (500 MHz, CDCl$_3$) δ 7.27 (app q, J=3.4 Hz, 1.8 Hz, 2H), 7.14 (s, 1H), 7.22 (s, 2H), 7.11 (m, 2H), 7.01 (d, J=8.9 Hz, 1H), 5.74 (s, 1H), 4.42 (d, J=5.9 Hz, 2H), 3.53 (app d, J=19.9 Hz, 2H), 3.23 (s, 2H), 3.15 (app d, J=19.9 Hz, 2H).

Step F

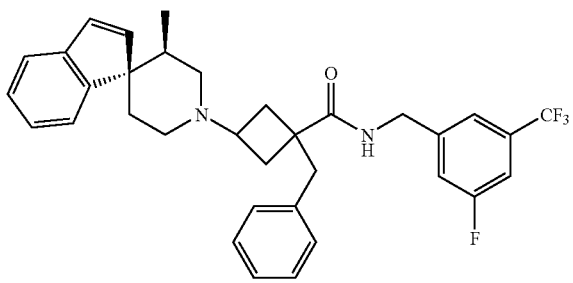

A solution of the product form Step E (40 mg, 0.11 mmol), Intermediate 2 (25 mg, 0.11 mmol), DIEA (28 µL, 0.16 mmol), 4 Å molecular sieves, NaBH(OAc)$_3$ (115 mg, 0.530 mmol) and DCM (5 mL) was stirred at room temperature overnight. The crude reaction was purified by preparative TLC (3:0.3:96.7, MeOH:NH$_4$OH:DCM) to yield the final product (57 mg, 96.1%). LC-MS for C$_{34}$H$_{34}$F$_4$N$_2$O MW calculated 562.26. Found 563.35.

A variety of compounds with different amine and alkyl substitution were prepared according to the procedures detailed in Example 67 utilizing different amines and alkyl halides. All of the components are either commercially available or are described in the Intermediates section. Cis and trans isomers for some of these compounds were separated by preparative TLC. These compounds are summarized in the table below.

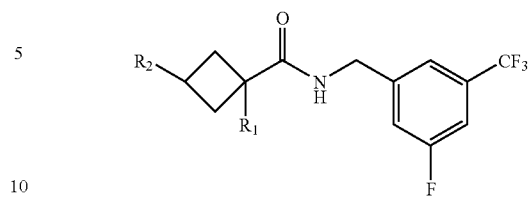

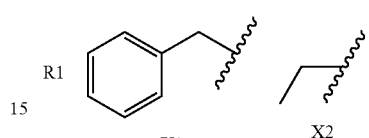

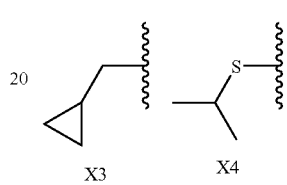

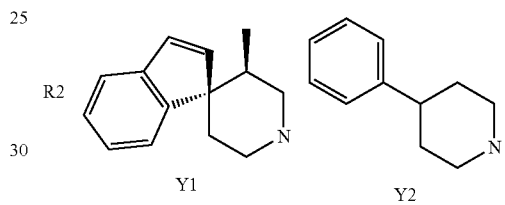

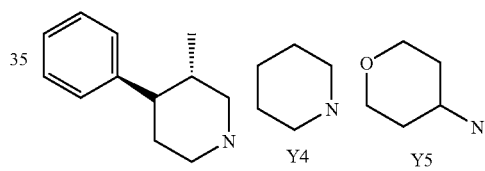

| Example | R1 | R2 | Molecular Formula | Calculated MW | Found [M+H+] |
|---|---|---|---|---|---|
| 68 | X1 | Y2 | C31H32F4N2O | 524.25 | 525.25 |
| 69 | X1 | Y4 | C25H28F4N2O | 448.21 | 449.2 |
| 70 | X2 | Y2 | C26H30F4N2O | 462.23 | 463.3 |
| 71 | X2 | Y4 | C20H26F4N2O | 386.20 | 387.2 |
| 72 | X3 | Y1 | C31H34F4N2O | 526.26 | 527.3 |
| 73 | X4 | Y1 | C30H34F4N2OS | 546.23 | 547.3 |
| 74 | X2 | Y3 | C27H32F4N2O | 476.25 | 477.25 |
| 75 | X2 | Y5 | C20H26F4N2O2 | 402.19 | 403.15 |
| 76 | X1 | Y5 | C25H28F4N2O2 | 464.21 | 465.25 |

EXAMPLE 77

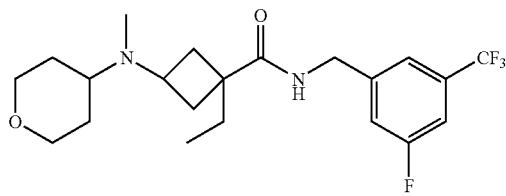

A solution of Example 75 (10 mg, 0.025 mmol), formaldehyde (6 µL, 0.08 mmol), DIEA (7 µL, 0.04 mmol), TFA (2.5 µL), NaCNBH (9 mg, 0.1 mmol), and MeOH (1/2 mL) was stirred at room temperature. The reaction was monitored by TLC. Upon completion of reaction, the reaction mixture was purified by preparative TLC (3:0.3:96.7, MeOH: NH$_4$OH:DCM) to yield Example 77 (6.2 mg, 60.2%). LC-MS for C$_{21}$H$_{28}$F$_4$N$_2$O$_2$ MW calculated 416.21. Found 417.25.

EXAMPLE 78

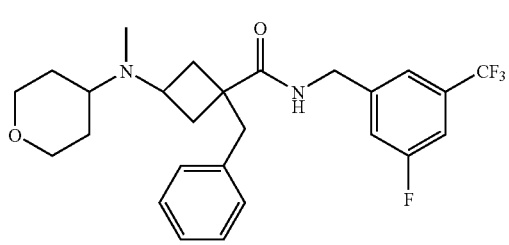

Example 78 was synthesized from Example 76 according to the procedure detailed in Example 77. The crude product was purified by preparative TLC (5:0.5:94.5, MeOH: NH$_4$OH:DCM). LC-MS for C$_{26}$H$_{30}$F$_4$N$_2$O$_2$ MW calculated 478.22. Found 479.35.

EXAMPLE 79

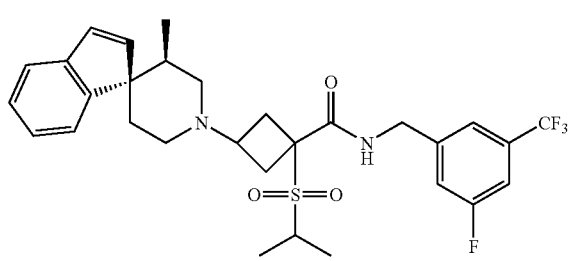

Step A

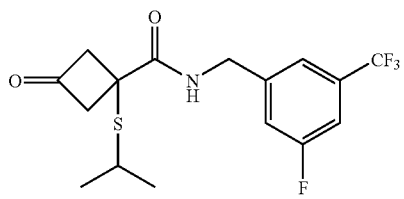

This intermediate was synthesized according to the procedure detailed in Example 67, Step A-E. Diisopropylsulfide was used as the alkylating agent in Step C. 1H NMR (500 MHz, CDCl$_3$) δ 7.53 (s, 1H), 7.37 (s, 1H), 3.28 (m, 1H), 7.23 (d, J=9.7 Hz, 1H), 4.56 (d, J=6.2 Hz, 2H), 3.93 (app d, J=19.7 Hz, 2H), 3.19 (app d, J=19.7 Hz, 2H), 2.96 (h J=6.8 Hz, 1H), 1.23 (d, J=6.6 Hz, 6H).

Step B

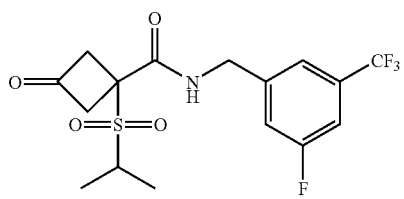

A solution of the product from Step A (120 mg, 0.331 mmol), iPrOH (5 mL), oxone (406 mg, 0.662 mmol) and water (5 mL) were stirred at room temperature. The reaction was monitored by HPLC. The mixture was concentrated in vacuo. The concentrate was redissolved in ether, washed with water (3×), dried over anhydrous MgSO$_4$, and concentrated to yield the crude product (100 mg, 76.3%). The crude product was used on next step.

Step C

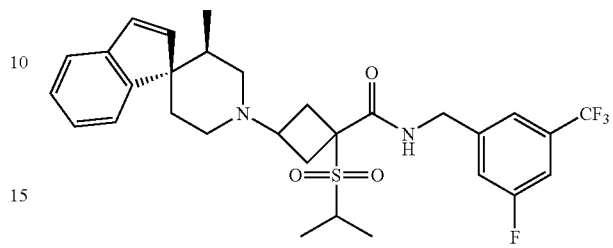

Example 79 was synthesized according to the procedure detailed in Example 67, Step F. LC-MS for C$_{30}$H$_{34}$F$_4$N$_2$O$_3$ MW calculated 578.22. Found 579.25.

EXAMPLE 80

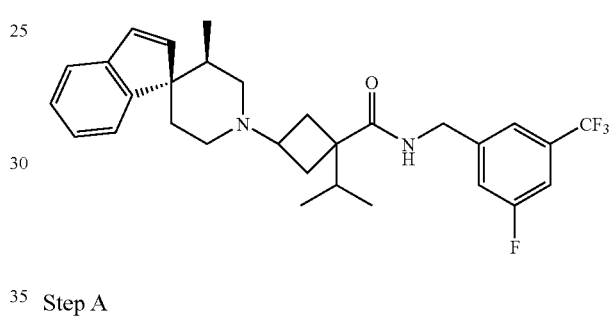

Step A

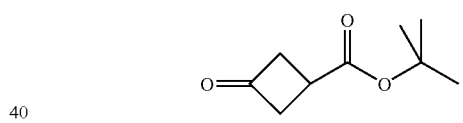

Concentrated sulfuric acid (5 mL, 90 mmol) was added to a vigorously stirred suspension of anhydrous MgSO$_4$ (42 g, 350 mmol) in DCM (250 μL). The mixture was stirred for 15 minutes before Intermediate 1 (10 g, 88 mmol) was added followed by tert-butanol (42.5 μL, 438 mmol). The reaction flask was stoppered tightly and stirred at room temperature for 60 hours. Saturated NaHCO$_3$ solution was added and the resulting mixture was stirred until the reaction mixture became clear as all MgSO$_4$ dissolved. The organic layer was separated and washed with brine, dried over anhydrous MgSO$_4$, and concentrated in vacuo. The crude product was used in next step.

Step B

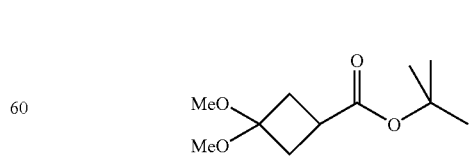

The product from Step A (15 g, 88 mmol) was dissolved in DCM (100 mL) and MeOH (100 mL) first before trimethyl orthoformate (96 mL, 880 mmol) was added. TsOH (1.7 g, 8.8 mmol) was added last. The reaction mixture was stirred at room temperature for 1 hour before being concentrated in vacuo. The concentrate was diluted with ether, quenched with saturated NaHCO3, washed with brine, dried over anhydrous MgSO$_4$, and concentrated to dryness. The crude product was purified by MPLC (10:90, EtOAc:hexanes) to yield the desired product (12.21 g, 64.3% for last two steps). 1H NMR (400 MHz, CDCl$_3$) δ 3.17 (d, J=6.4 Hz, 6H), 2.80 (p, J=8.8 Hz, 1H), 2.43-2.31 (m, 4H), 1.47 (s, 9H).

Step C

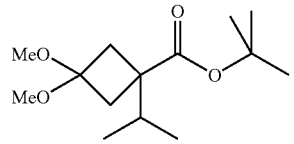

To a flamed-dried flask under nitrogen, iPr$_2$N (5.2 mL, 37 mmol) was added to THF (100 mL) at −78° C. followed by nBuLi (14.9 mL, 37.2 mmol) and the product from Step B (7.0 g, 32 mmol). The mixture was stirred for 30 minutes before 2-iodopropane (9.7 mL, 97 mmol) was added. The reaction was stirred at −78° C. for 1 hour before being placed in a freezer (−15° C.) for 18 hours. The solution was quenched with 10% citric acid (50 mL) and extracted with ether (3×). Combined organic layer was washed with water and brine, dried over anhydrous MgSO$_4$, and concentrated in vacuo. The crude product was purified by MPLC (7.5:92.5, EtOAc:hexanes) to yield the desired product (5.16 g, 61.7%). 1H NMR (500 MHz, CDCl$_3$) δ 3.13 (s, 6H), 2.57 (app d, J=13.5 Hz, 2H), 2.01 (app d, J=13.3 Hz, 2H), 1.90 (h, J=6.9 Hz, 1H), 1.47 (s, 9 H), 0.91 (d, J=6.8 Hz, 6H).

Step D

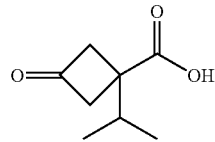

The product from Step C (5.2 g, 20 mmol) was dissolved in 20% HCl (30 mL). The reaction mixture was heated to reflux for 60 hours before being cooled to room temperature. Ether was added and the solution was vigorously stirred for 24 hours. The ether layer was separated and the aqueous layer was further extracted with ether (3×). The combined organic layers were dried over anhydrous MgSO$_4$ and concentrated in vacuo to yield the desired white solid product (2.46 g, 78.8%). 1H NMR (500 MHz, CDCl3) δ 3.52 (app d, J=20.9 Hz, 2H), 3.15 (app d, J=20.8 Hz, 2H), 2.29 (p, J=6.9 Hz, 1H), 1.08 (d, J=6.9 Hz, 6H).

Step E

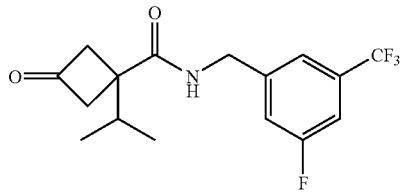

A solution of the product from Step D (300 mg, 1.92 mmol), 3-fluoro-5-trifluoromethylbenzylamine (280 µL, 1.92 mmol), HOAT (260 mg, 1.92 mmol), EDC (550 mg, 2.89 mmol), and DCM (20 mL) was stirred at room temperature overnight. The reaction was diluted with DCM, washed with 1 M HCl solution, saturated NaHCO$_3$, water (2×) and brine, dried over anhydrous MgSO$_4$, and concentrated in vacuo. The crude product was purified by preparative TLC (20:80, EtOAc:hexanes) to yield the desired product (444 mg, 69.8%). 1H NMR (400 MHz, CDCl$_3$) δ 7.36 (s, 1H), 7.29-7.22 (m, 2H), 5.99 (s, 1H), 4.57 (d, J=6.0 Hz, 2H), 3.44 (app d, J=20.1 Hz, 2H), 3.05 (app d, J=20.3 Hz, 2H), 2.14 (h, J=6.8 Hz, 1H), 1.03 (d, J=6.8 Hz, 6H).

Step F

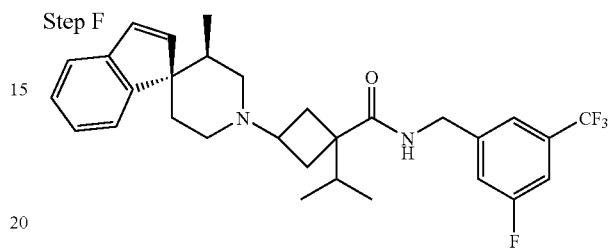

A solution of the product from Step E (50 mg, 0.13 mmol), Intermediate 2 (32 mg, 0.13 mmol), DIEA (25 µL, 0.13 mmol), 4 Å molecular sieves, NaBH(OAc)$_3$ (110 mg, 0.52 mmol) and DCM (7 mL) was stirred at room temperature overnight. The crude reaction was purified by preparative TLC (3:0.3:96.7, MeOH:NH$_4$OH:DCM) to yield Example 80 (36 mg, 46.4%). LC-MS for C$_{30}$H$_{34}$F$_4$N$_2$O MW calculated 514. Found 515.

A variety of compounds were synthesized according to the procedure detailed in Example 80. R2 was derivatized by using either 2-iodoprotane or acetone as the alkylating agent in Step C. R1 was derivatized by using different benzylamine in Step E. 1.5 equivalent of DIEA was added for hydrochloride benzylamine. R3 was derivatized by incorporating different amines in Step F. All of the components are either commercially available or are described in the Intermediates section. Isomers for some of these compounds were separated by preparative TLC. A few most active ones were resolved using chiral chromatography. A summary of these compounds is listed in the table below.

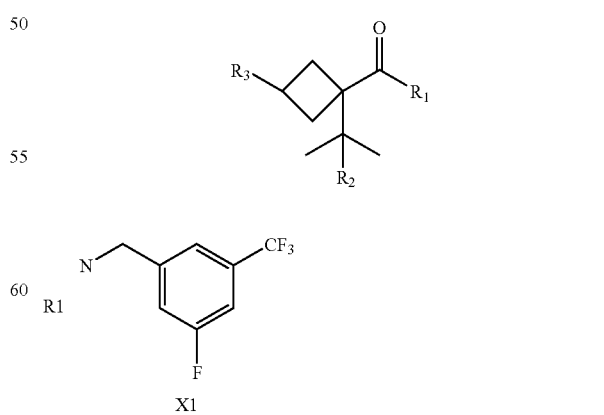

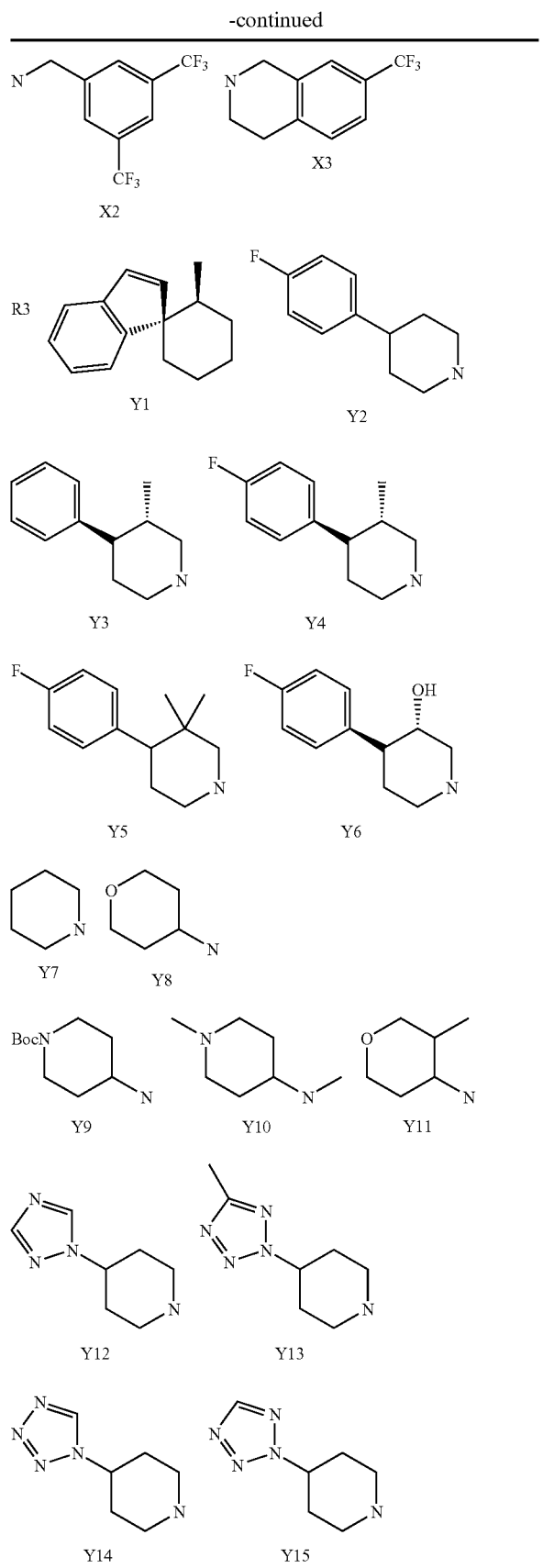

| Example | R1 | R2 | R3 | Molecular Formula | Calculated MW | Found [M+H+] |
|---|---|---|---|---|---|---|
| 81 | X1 | H | Y2 | C27H31F5N2O | 494 | 495 |
| 82 | X1 | H | Y3 | C28H34F4N2O | 490 | 491 |
| 83 | X1 | H | Y7 | C21H28F4N2O | 400 | 401 |
| 84 | X1 | H | Y8 | C21H28F4N2O2 | 416 | 417 |
| 85 | X1 | H | Y9 | C26H37F4N3O3 | 515 | 516 |
| 86 | X1 | H | Y10 | C23H33F4N3O | 443 | 444 |
| 87 | X2 | H | Y1 | C31H34F6N2O | 564 | 565 |
| 88 | X2 | H | Y2 | C28H31F7N2O | 544.23 | 545.2 |
| 89 | X2 | H | Y3 | C29H34F6N2O | 540 | 541 |
| 90 | X2 | H | Y7 | C22H28F6N2O | 450 | 451 |
| 91 | X2 | H | Y8 | C22H28F6N2O2 | 466 | 467 |
| 92 | X2 | H | Y9 | C27H37F6N3O3 | 565 | 566 |
| 93 | X2 | H | Y10 | C24H33F6N3O | 493 | 494 |
| 94 | X1 | OH | Y1 | C30H34F4N2O2 | 530.26 | 531.25 |
| 95 | X1 | OH | Y8 | C21H28F4N2O3 | 432.20 | 433.15 |
| 96 | X2 | OH | Y1 | C31H34F6N2O2 | 580.25 | 581.2 |
| 97 | X2 | OH | Y8 | C22H28F6N2O3 | 482.20 | 483.25 |
| 98 | X2 | OH | Y2 | C28H31F7N2O2 | 560.23 | 561.25 |
| 99 | X2 | H | Y12 | C24H29F6N5O | 517.23 | 518.2 |
| 100 | X2 | H | Y13 | C24H30F6N6O | 532.24 | 533.2 |
| 101 | X2 | H | Y14 | C23H28F6N2O | 518.22 | 519.25 |
| 102 | X2 | H | Y15 | C23H28F6N6O | 518.22 | 519.25 |
| 103 | X2 | H | Y16 | C24H29F6N5O | 517.23 | 518.2 |
| 104 | X2 | H | Y17 | C24H29F6N5O | 517.23 | 518.2 |
| 105 | X3 | H | Y1 | C32H37F3N2O | 522.29 | 523.45 |
| 106 | X3 | H | Y8 | C23H31F3N2O2 | 424.23 | 525.35 |
| 107 | X1 | OH | Y4 | C28H33F5N2O2 | 524.25 | 525.25 |
| 108 | X2 | OH | Y4 | C29H33F7N2O2 | 574.24 | 575.2 |
| 109 | X2 | H | Y5 | C30H35F7N2O | 572.25 | 573.25 |
| 110 | X2 | H | Y4 | C29H33F7N2O | 558.25 | 559.3 |
| 111 | X2 | H | Y6 | C28H31F7N2O3 | 576.22 | 577.3 |
| 112 | X1 | OH | Y5 | C29H35F5N2O2 | 538.25 | 539.35 |
| 113 | X1 | OH | Y6 | C27H31F5N2O3 | 526.23 | 527.3 |
| 114 | X2 | OH | Y5 | C30H35F7N2O2 | 588.24 | 589.3 |
| 115 | X2 | OH | Y6 | C28H31F7N2O2 | 560.23 | 561.25 |
| 116 | X2 | OH | Y11 | C23H30F6N2O3 | 496.22 | 497.35 |

EXAMPLE 117

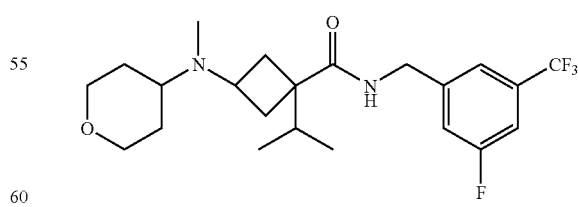

A solution of Example 83 (40 mg, 0.10 mmol), 37% formaldehyde (25 μL, 0.30 mmol), DIEA (23 μL, 0.15 mmol), TFA (10 μL), NaCNBH (28 mg, 0.50 mmol), and MeOH (3 mL) was stirred at room temperature and the reaction was monitored by TLC. The crude reaction was purified by preparative TLC (5:0.5:94.5, MeOH:NH₄OH:DCM). LC-MS for $C_{22}H_{30}F_4N_2O_2$ MW calculated 430. Found 431.

EXAMPLE 118

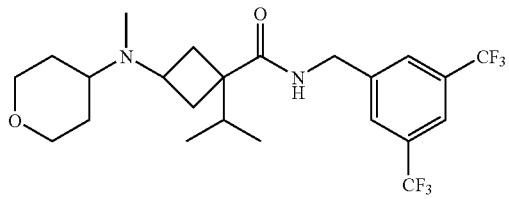

Example 118 was synthesized from Example 91 using the procedure detailed in Example 117. LC-MS for $C_{23}H_{30}F_4N_2O_2$ MW calculated 480. Found 481.

EXAMPLE 119

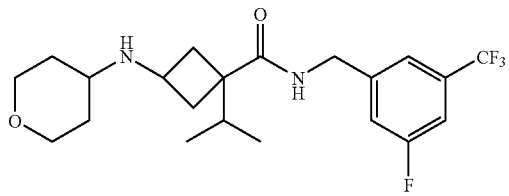

Example 85 (15 mg, 0.029 mmol) was stirred in 4 M HCl in dioxane (5 mL). The reaction was monitored by HPLC. Upon completion of reaction, the mixture was concentrated in vacuo to yield Example 119. LC-MS for $C_{21}H_{29}F_4N_3O_2$ MW calculated 415. Found 416.

EXAMPLE 120

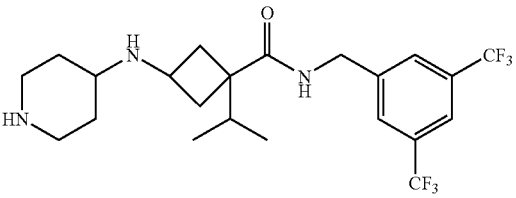

Example 120 was synthesized from Example 92 using the procedure detailed in Example 119. LC-MS for $C_{22}H_{29}F_6N_3O$ MW calculated 465. Found 466.

EXAMPLE 121

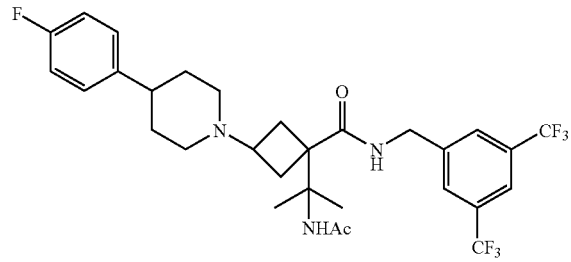

Concentrated sulfuric acid (2 mL) was cooled to 0° C. before a solution of Example 98 (55 mg, 0.098 mmol) in acetonitrile (700 µL) was added. The mixture was stirred at room temperature overnight. The reaction was poured onto ice slowly, made basic with 5 M NaOH, and extracted with ether (3×). Combined organic layer was dried over anhydrous MgSO₄ and concentrated in vacuo. The crude product was purified by preparative TLC (1:0.1:98.9, MeOH:NH₄OH:EtOAc) to yield Example 121. Cis and trans isomers were also separated (total yield 30 mg, 54.2%). LC-MS for $C_{30}H_{34}F_7N_3O_2$ MW calculated 601.25. Found 602.

EXAMPLE 122

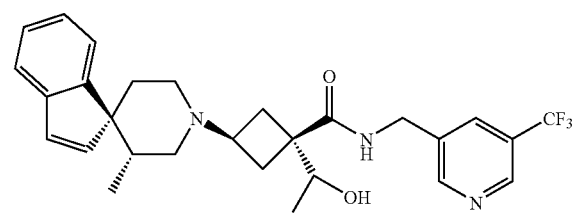

Step A

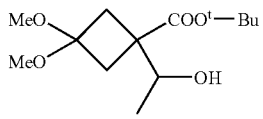

To a solution of diisopropylamine (1.1 mL, 7.7 mmol) in THF (20 mL) was added BuLi (1.6 M in hexane, 4.2 mL) at −15° C. After 15 minutes, the reaction was cooled to −78° C. and the product from Example 80, Step B was added dropwise. The solution was stirred at −78° C. for another 30 minutes before a solution of acetaldehyde (437 µL, 7.74 mmol) in THF (5 mL) was added. The reaction was further stirred at −78° C. for 10 minutes before being quenched by pouring into a saturated NaHCO₃ aqueous solution (120 mL). The aqueous layer was extracted with ether three times and the organic layers were combined, washed with brine, dried over Na₂SO₄, concentrated and purified by flash chromatography (20% EtOAc/hexane) to give the product as a colorless oil. 1H NMR (500 MHz, CDCl₃) δ 3.92-3.87 (m, 1H), 3.15 (s, 6H, OMe), 2.79 (d, J=8.0 Hz, 1H), 2.62 (d, J=9.0 Hz, 1H), 2.10-2.00 (m, 2H), 1.50 (s, 9H), 1.12 (d, J=6.4 Hz, 3H, CH₃), LC-MS for $C_{13}H_{24}O_5Na$ [M+Na⁺]: calculated 283.16. Found 283.1.

Step B

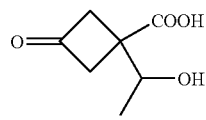

To the product from Step A was added 20% TFA/CH₂Cl₂ (15 mL) at room temperature. The reaction was stirred for 3 hours before acetone (1 mL) and water (500 µL) was added. The reaction was further stirred for 1 hour before being concentrated in vacuo to afford the desired ketone acid (457 mg, 94%) as foaming solid. 1H NMR (500 MHz, CDCl₃) δ 4.25 (q, J=6.4 Hz, 1H), 3.60-3.42 (m, 2H), 3.35-3.25 (m, 1H), 3.22-3.15 (m, 1H), 1.40 (d, J=6.4 Hz, 3H).

Step C

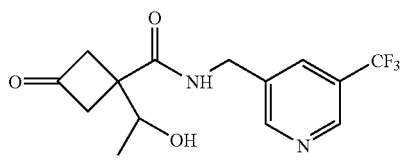

To a mixture of The product from Step B (171 mg, 1.08 mmol), 2-trifluoro-4-aminomethyl-pyridine (230 mg, 1.08 mmol), EDC (311 mg, 1.62 mmol) and HOBT (220 mg, 1.62 mmol) was added anhydrous $CH_2Cl_2$ (5 mL) followed by DIEA (377 μL, 2.16 mmol). The reaction was stirred at room temperature overnight and then concentrated in vacuo. The resulted oil was purified by flash chromatography (85% EtOAc/hexane) to give the desired product (195 mg, 57%) as white solid. LC-MS for $C_{14}H_{16}F_3N_2O_3$ [M+H$^+$]: calculated 317.10. Found 317.1.

Step D

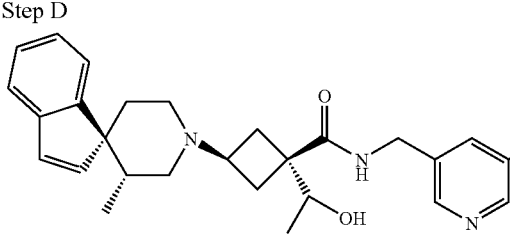

To a solution of the product from Step C (23 mg, 0.072 mmol) and Intermediate 2 (25 mg, 0.11 mmol) in $CH_2Cl_2$ (1 mL) was added DIEA (14 μL, 0.080 mmol) followed by $NaBH(OAc)_3$ (25 mg, 0.12 mmol). The reaction was stirred at room temperature overnight before being concentrated to a crude oil. This oil was purified by reverse phase HPLC (MetaChem Polaris C18-A 5 micron, 15% to 80% $CH_3CN$/$H_2O$/0.1% TFA) to give a cis racemate (20 mg) and a trans racemate (15 mg). The cis isomer was the less polar peak and the more active isomer. The cis isomer was further separated by chiral HPLC (AD, 10% EtOH/heptane) to give two enantiomers. LC-MS for $C_{28}H_{33}F_3N_3O_2$ [M+Na$^+$]: calculated 500.24. Found 500.25.

A variety of compounds were synthesized according to the procedure detailed in Example 122. R1 was derivatized by using either 2-iodopropane or acetone as the alkylating agent in Step A. R2 was derivatized by using a different amine in Step C. R3 was derivatized by incorporating different amines. All of the components are either commercially available or are described in the Intermediates section. Isomers for some of these compounds were separated by reverse-phase HPLC. Some of these compounds were resolved into their individual stereoisomers using chiral chromatography. A summary of these compounds is listed in the table below.

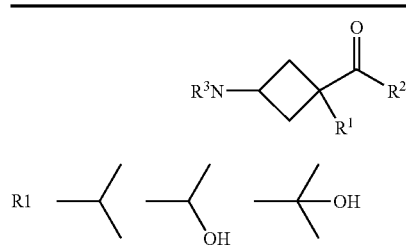

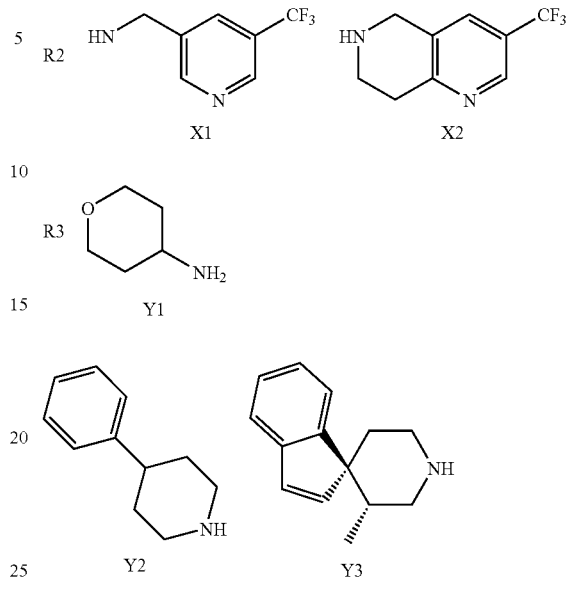

| Example | R1 | R2 | R3 | Molecular formula | Calculated MW | Found [M + H]$^+$ |
|---|---|---|---|---|---|---|
| 123 | i-Pr | X1 | Y1 | C20H28F3N3O2 | 399.21 | 400.2 |
| 124 | i-Pr | X1 | Y2 | C26H32F3N3O | 459.25 | 460.5 |
| 125 | i-Pr | X1 | Y3 | C29H34F3N3O | 497.27 | 498.2 |
| 126 | i-Pr | X2 | Y1 | C22H30F3N3O2 | 425.23 | 426.2 |
| 127 | i-Pr | X2 | Y2 | C28H34F3N3O | 485.27 | 486.3 |
| 128 | i-Pr | X2 | Y3 | C31H36F3N3O | 523.28 | 524.3 |
| 129 | CH(OH)CH3 | X1 | Y1 | C19H26F3N3O3 | 401.19 | 402.1 |
| 130 | CH(OH)CH3 | X1 | Y2 | C25H30F3N3O2 | 461.23 | 462.5 |
| 131 | CH(OH)CH3 | X1 | Y3 | C28H32F3N3O2 | 499.24 | 500.25 |
| 132 | CH(OH)CH3 | X2 | Y1 | C21H28F3N3O3 | 427.21 | 428.2 |
| 133 | CH(OH)CH3 | X2 | Y2 | C27H32F3N3O2 | 487.24 | 488.15 |
| 134 | CH(OH)CH3 | X2 | Y3 | C30H34F3N3O2 | 525.26 | 526.3 |
| 135 | C(OH)(CH3)2 | X1 | Y1 | C20H28F3N3O3 | 415.21 | 416.2 |
| 136 | C(OH)(CH3)2 | X1 | Y2 | C26H32F3N3O2 | 475.24 | 476.5 |
| 137 | C(OH)(CH3)2 | X1 | Y3 | C29H34F3N3O2 | 513.26 | 514.25 |
| 138 | C(OH)(CH3)2 | X2 | Y1 | C22H30F3N3O3 | 441.22 | 442.2 |
| 139 | C(OH)(CH3)2 | X2 | Y2 | C28H34F3N3O2 | 501.26 | 502.25 |
| 140 | C(OH)(CH3)2 | X2 | Y3 | C31H36F3N3O2 | 539.28 | 540.3 |

What is claimed is:

1. A compound of formula IIa:

[Structural formula IIa shown with R⁹, R⁷, R⁸, X, R¹⁰ on a piperidine-like ring connected via N to a cyclobutane bearing R¹ and a C(O)NH-CH₂-phenyl group with R⁵ and Z-R³ substituents]

wherein:

X is C;

$R^{11}$ is selected from: hydroxy, hydrogen, $C_{1-6}$alkyl, —O—$C_{1-6}$alkyl, benzyl, phenyl and $C_{3-6}$cycloalkyl, where said alkyl, phenyl, benzyl and cycloalkyl groups are unsubstituted or substituted with 1-3 substituents, and where said substituents are independently selected from: halo, hydroxy, $C_{1-3}$alkyl, $C_{1-3}$alkoxy, —$CO_2H$, —$CO_2$—$C_{1-6}$alkyl and trifluoromethyl;

$R^{12}$ is selected from: hydrogen, $C_{1-6}$ alkyl, benzyl, phenyl and $C_{3-6}$cycloalkyl, where said alkyl, phenyl, benzyl and cycloalkyl groups are unsubstituted or substituted with 1-3 substituents, and where said substituents are independently selected from: halo, hydroxy, $C_{1-3}$alkyl, $C_{1-3}$alkoxy, —$CO_2H$, —$CO_2$—$C_{1-6}$alkyl, and trifluoromethyl;

$R^{13}$ is selected from: hydrogen, $C_{1-6}$alkyl, —O—$C_{1-6}$ alkyl, benzyl, phenyl and $C_{3-6}$cycloalkyl, where said alkyl, phenyl, benzyl and cycloalkyl groups are unsubstituted or substituted with 1-3 substituents, and where said substituents are independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{14}$ is selected from: hydroxy, $C_{1-6}$ alkyl, —O—$C_{1-6}$alkyl, benzyl, phenyl, and $C_{3-6}$cycloalkyl, where said alkyl, phenyl, benzyl and cycloalkyl groups are unsubstituted or substituted with 1-3 substituents, and where said substituents are independently selected from: halo, hydroxy, $C_{1-3}$alkyl, $C_{1-3}$alkoxy, —$CO_2H$, —$CO_2$—$C_{1-6}$ alkyl and trifluoromethyl;

Z is selected from C and N;

$R^1$ is selected from:
(a) hydrogen,
(b) —$C_{1-6}$alkyl,
(c) —$C_{0-6}$alkyl-O—$C_{1-6}$alkyl,
(d) —$C_{0-6}$alkyl-S—$C_{1-6}$alkyl,
(e) —($C_{0-6}$alkyl)-($C_{3-7}$cycloalkyl)-($C_{0-6}$alkyl),
(f) hydroxy,
(g) heterocycle,
(h) —CN,
(i) —$NR^{12}R^{12}$,
(j) —$NR^{12}COR^{13}$,
(k) —$NR^{12}SO_2R^{14}$,
(l) —$COR^{11}$,
(m) —$CONR^{12}R^{12}$, and
(n) phenyl;

where said alkyl and cycloalkyl are unsubstituted or substituted with 1-7 substituents, and where said substituents are independently selected from: halo, hydroxy, —O—$C_{1-3}$alkyl, trifluoromethyl, $C_{1-3}$alkyl, —$COR^{11}$, —$SO_2R^{14}$, —$NHCOCH_3$, —$NHSO_2CH_3$, -heterocycle, =O, —CN, and where said phenyl and heterocycle are unsubstituted or substituted with 1-3 substituents where the substituents are independently selected from: halo, hydroxy, —$COR^{11}$, $C_{1-3}$alkyl, $C_{1-3}$alkoxy and trifluoromethyl;

$R^3$ is selected from:
(a) hydrogen,
(b) $C_{1-3}$alkyl, optionally substituted with 1-3 fluoro,
(c) —O—$C_{1-3}$alkyl, optionally substituted with 1-3 fluoro,
(d) hydroxy,
(e) chloro,
(f) fluoro,
(g) bromo,
(h) phenyl,
(i) heterocycle, and
(j) nothing or O (when the Z bonded to $R^3$ is N);

$R^5$ is selected from:
(a) $C_{1-6}$alkyl, where alkyl is unsubstituted or substituted with 1-6 fluoro and optionally substituted with hydroxyl,
(b) —O—$C_{1-6}$alkyl, where alkyl is unsubstituted or substituted with 1-6 fluoro,
(c) —CO—$C_{1-6}$alkyl, where alkyl is unsubstituted or substituted with 1-6 fluoro,
(d) —S—$C_{1-6}$alkyl, where alkyl is unsubstituted or substituted with 1-6 fluoro,
(e) -pyridyl, which is unsubstituted or substituted with one or more substituents selected from: halo, trifluoromethyl, $C_{1-4}$alkyl, and $COR^{11}$,
(f) fluoro,
(g) chloro,
(h) bromo,
(i) —$C_{4-6}$cycloalkyl,
(j) —O—$C_{4-6}$cycloalkyl,
(k) phenyl, which is unsubstituted or substituted with one or more substituents selected from: halo, trifluoromethyl, $C_{1-4}$alkyl, and $COR^{11}$,
(l) —O-phenyl, which is unsubstituted or substituted with one or more substituents selected from: halo, trifluoromethyl, $C_{1-4}$alkyl, and $COR^{11}$,
(m) —$C_{3-6}$cycloalkyl, where alkyl is unsubstituted or substituted with 1-6 fluoro,
(n) —O—$C_{3-6}$cycloalkyl, where alkyl is unsubstituted or substituted with 1-6 fluoro,
(o) -heterocycle,
(p) —CN, and
(q) —$COR^{11}$;

$R^7$ and $R^8$ are joined together to form a ring which is selected from:
(a) 1H-indene,
(b) 2,3-dihydro-1H-indene,
(c) 2,3-dihydro-benzofuran,
(d) 1,3-dihydro-isobenzofuran,
(e) 2,3-dihydro-benzothiofuran,
(f) 1,3-dihydro-isobenzothiofuran,
(g) 6H-cyclopenta[d]isoxazol-3-ol
(h) cyclopentane, and
(i) cyclohexane, where the ring formed is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$, and —$C_{0-3}$-heterocycle, and $R^9$ and $R^{10}$ are independently selected from:
(a) hydrogen,
(b) hydroxy,
(c) $C_{1-6}$alkyl,
(d) $C_{1-6}$alkyl-$COR^{11}$, (e) $C_{1-6}$alkyl-hydroxy,
(f) —O—$C_{1-3}$alkyl, and
(g) halo;
or a pharmaceutically acceptable salt or individual diastereomer thereof.

2. The compound of claim 1 of formula IId:

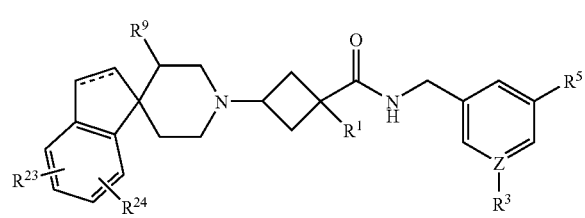

IId wherein the dashed line represents a single or a double bond, and $R^{23}$ and $R^{24}$ are independently selected from:
(a) hydrogen,
(b) halo,
(c) trifluoromethyl,
(d) hydroxy,
(e) $C_{1-3}$alkyl,
(f) —O—$C_{1-3}$alkyl,
(g) —$C_{0-3}$—$CO_2H$,
(h) —$C_{0-3}$—$CO_2C_{1-3}$alkyl,
(i) —CN, and
(j) —$C_{0-3}$—heterocycle,
or a pharmaceutically acceptable salt or individual diastereomer thereof.

3. The compound of claim 2 of formula IIf:

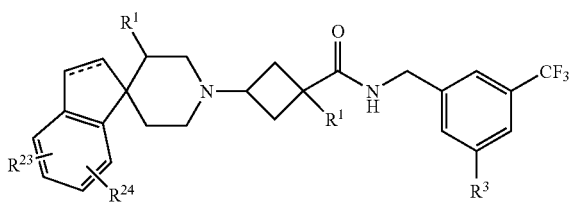

IIf or a pharmaceutically acceptable salt or individual diastereomer thereof.

4. The compound of claim 3 wherein $R^1$ is selected from: hydrogen, phenyl, heterocycle, —$C_{1-6}$alkyl, —$C_{0-6}$alkyl-O—$C_{1-6}$alkyl, and —($C_{0-6}$alkyl)-($C_{3-7}$cycloalkyl)-($C_{0-6}$alkyl),
where said alkyl, phenyl, heterocycle, and cycloalkyl are unsubstituted or substituted with 1-7 substituents, where said substituents are independently selected from:
(a) halo,
(b) hydroxy,
(c) —O—$C_{1-3}$alkyl,
(d) trifluoromethyl,
(f) $C_{1-3}$alkyl,
(g) —O—$C_{1-3}$alkyl,
(h) —$COR^{11}$,
(i) —CN,
(j) —$NR^{12}R^{12}$, and
(k) —$CONR^{12}R^{12}$.

5. The compound of claim 4 wherein $R^1$ is selected from:
(1) —$C_{1-6}$alkyl, which is unsubstituted or substituted with 1-6 substituents where said substituents are independently selected from:
(a) halo,
(b) hydroxy,
(c) —O—$C_{1-3}$alkyl,
(d) trifluoromethyl, and
(e) —$COR^{11}$,
(2) —$C_{0-6}$alkyl-O—$C_{1-6}$alkyl-, which is unsubstituted or substituted with 1-6 substituents where said substituents are independently selected from:
(a) halo,
(b) trifluoromethyl, and
(c) —$COR^{11}$,
(3) —($C_{3-5}$cycloalkyl)-($C_{0-6}$alkyl), which is unsubstituted or substituted with 1-7 substituents where said substituents are independently selected from:
(a) halo,
(b) hydroxy,
(c) —O—$C_{1-3}$alkyl,
(d) trifluoromethyl, and
(e) —$COR^{11}$,
(4) phenyl or heterocycle which is unsubstituted or substituted with 1-3 substituents where said substituents are independently selected from:
(a) halo,
(b) hydroxy,
(c) —O—$C_{1-3}$alkyl,
(d) trifluoromethyl, and
(e) —$COR^{11}$.

6. The compound of claim 5 wherein $R^1$ is selected from:
(a) hydrogen,
(b) $C_{-1-6}$alkyl, which is unsubstituted or substituted with 1-6 substituents independently selected from: fluoro and hydroxyl
(c) phenyl, and
(d) pyridyl.

7. The compound of claim 2 wherein Z is C and $R^3$ is selected from:
(a) hydrogen
(b) halo
(c) hydroxy
(d) $C_{1-3}$alkyl, where the alkyl is unsubstituted or substituted with 1-6 substituents independently selected from: fluoro, and hydroxy,
(e) —$COR^{11}$,
(f) —$CONR^{12}R^{12}$,
(g) -heterocycle,
(h) —$NR^{12}$—$SO_2$—$NR^{12}R^{12}$,
(i) —$NR^{12}$—$SO_2$—$R^{14}$,
(j) —$SO_2$—$NR^{12}R^{12}$,
(k) -nitro, and
(l) —NR12R12.

8. The compound of claim 7 wherein Z is C and $R^3$ is selected from:
(a) fluoro,
(b) trifluoromethyl, and
(c) hydrogen.

9. The compound of claim 2 wherein $R^5$ is selected from:
(a) $C_{1-6}$alkyl substituted with 1-6 fluoro,
(b) —O—$C_{1-6}$alkyl substituted with 1-6 fluoro,
(c) chloro,
(d) bromo, and
(e) phenyl.

10. The compound of claim 1, which is selected from the following compounds, or a pharmaceutically acceptable salt or individual diastereomer thereof:

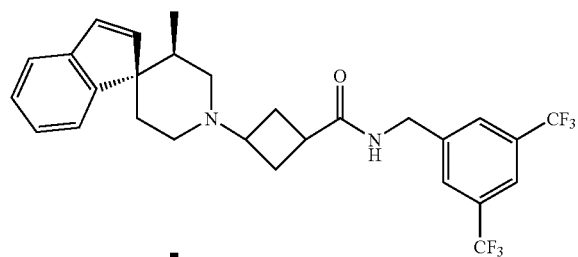

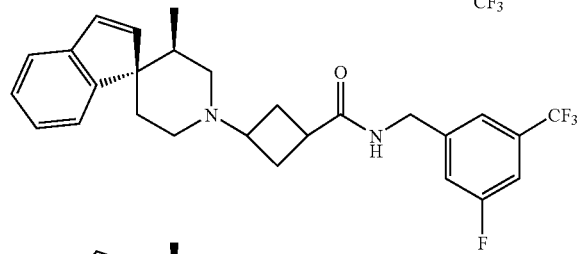

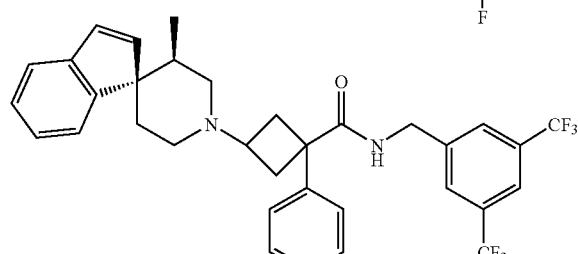

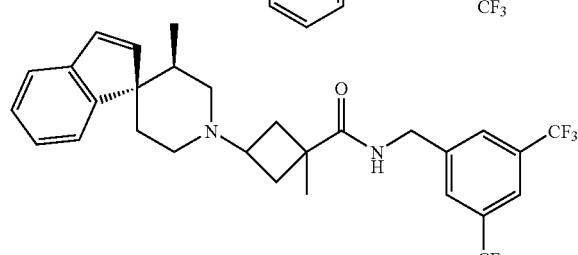

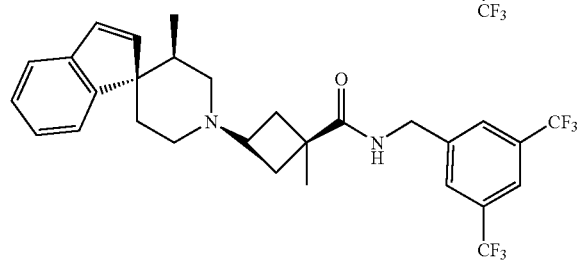

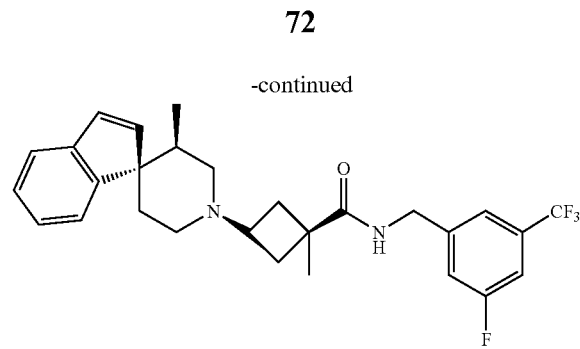

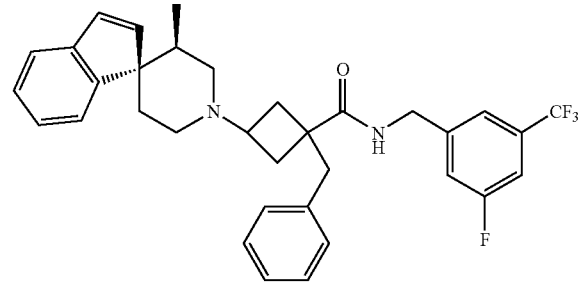

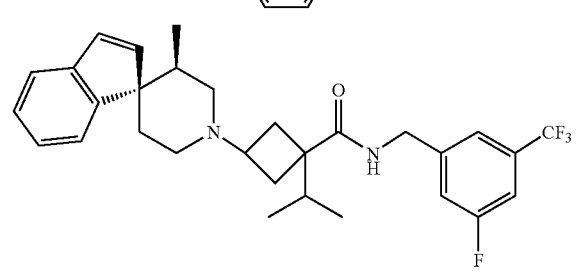

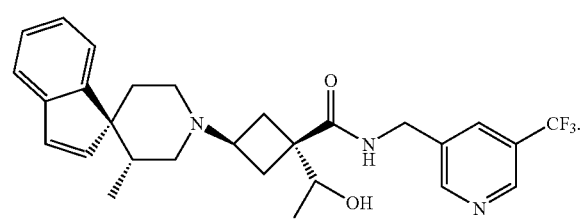

11. A pharmaceutical composition which comprises an inert carrier and a compound of claim 1.

12. A method for treating rheumatoid arthritis which comprises the administration to a patient of an effective amount of the compound of claim 1.

* * * * *